(12) United States Patent
Hansen

(10) Patent No.: US 6,924,082 B1
(45) Date of Patent: Aug. 2, 2005

(54) DOUBLE-BOND SHIFTS OF SUBSTITUTED (4N)-ANNULENES FOR INFORMATION STORAGE AND DATA PROCESSING

(75) Inventor: Hans-Jürgen Hansen, Zürich (CH)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 0 days.

(21) Appl. No.: 09/319,566

(22) PCT Filed: Dec. 10, 1996

(86) PCT No.: PCT/IB96/01410

§ 371 (c)(1),
(2), (4) Date: Aug. 9, 1999

(87) PCT Pub. No.: WO98/26412

PCT Pub. Date: Jun. 18, 1998

(51) Int. Cl.[7] .............................. G11B 7/24; C07C 69/76

(52) U.S. Cl. .......................... 430/270.15; 430/1; 430/2; 430/290; 430/945; 385/21; 560/47; 560/102; 560/103; 560/28; 560/8

(58) Field of Search ................................. 430/1, 2, 290, 430/945, 270, 15; 385/21; 560/47, 102, 103, 28, 8

(56) References Cited

U.S. PATENT DOCUMENTS 5,432,873 A * 7/1995 Hosoya et al. ................. 385/21
5,438,561 A * 8/1995 Van et al. ...................... 360/100

FOREIGN PATENT DOCUMENTS

JP        A-59182460        10/1984

OTHER PUBLICATIONS

Caulfield, H.J., et al., "The Apllication of Holography", pp. 30–33, 1970.*

Rhodes, C.J., J. Chem. Soc., Chem. Commun., pp. 592–593, 1990.*
Weber, et al., Helvetica Chimica Acta, vol. 70, pp. 1439–1460, 1987.*
Hanzawa, et al., J. Am. Chem. Soc., vol. 103(9) pp. 2269–2272, 1981.*
Paquette, L.A., Pure & Appl. Chem., vol. 54(5) pp. 987–1004, 1982.*
Hafner, K., et al., Pure & Appl. Chem., vol. 65(1) pp. 17–25, 1993.*
Hafner, K., et al., Bull. Chem. Soc. Jpn., vol. 61. Pp. 155–163, 1988.*
Anger, I., et al., J. Phys. Chem., vol. 99, pp. 650–652, 1995.*
Bernhard et al., *Helvetica Chimica Acta*, 68:429–438 (1985).
Briquet et al., *Helvetica Chimica Acta*, 77:1940–1968 (1994).
Briquet et al., *Helvetica Chimica Acta*, 79:2282–2315 (1996).
El Houar et al., *Chimia*, vol. 50, No. 7/8, p. 341, abstract 151 (1996).

(Continued)

Primary Examiner—Martin Angebranndt
(74) Attorney, Agent, or Firm—JoAnn Villamizar

(57) ABSTRACT

The present application describes a method for information storage and data processing comprising the steps of thermo inducing or photo inducing double-bond shifts (DBS) in substituted (4n)-annulenes thus generating transitions between two different conjugation states with at least one substituent. The two different conjugation states are the conjugation on-state and conjugation off-state of the annulene core π-electrons with the substituent π-electrons. The present invention is furthermore related to novel substituted (4n)-heptalenes being optically and/or thermally switchable, based on thermal or photochemical double-bond shifts (DBS) as well as methods for their preparation. The (4n)-heptalenes can be used for information storage and data processing devices.

24 Claims, 2 Drawing Sheets

OTHER PUBLICATIONS

Figure 1A:
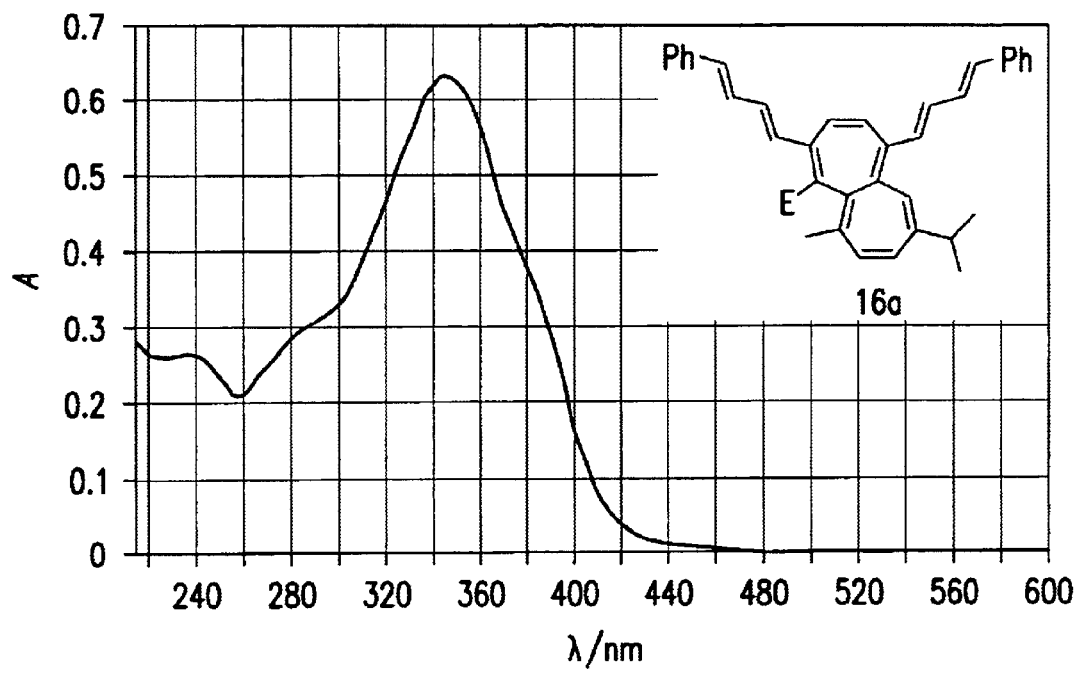

Gottarelli et al., *Helvetica Chimica Acta*, 70:430–435 (1987).

Hafner et al., *Tetrahedron Letters*, vol. 27, No. 15, pp. 1669–1672 (1986).

Hafner et al., *Tetrahedron Letters*, vol. 27, No. 15, pp. 1673–1676 (1986).

Weber et al., *Helvetica Chimica Acta*, 70:742–759 (1987).

* cited by examiner

US 6,924,082 B1

DOUBLE-BOND SHIFTS OF SUBSTITUTED (4N)-ANNULENES FOR INFORMATION STORAGE AND DATA PROCESSING

FIELD OF THE INVENTION

The present invention is related to a method for information storage and data processing comprising the step of thermo inducing or photo inducing double-bond shifts (DBS) in substituted [4n]-annulenes thus generating transitions between two different conjugation states with at least one substituent. The two different conjugation states are the conjugation on-state and conjugation off-state of the annulene core π-electrons with the substituent π-electrons.

The present invention is furthermore related to novel substituted [4n]-heptalenes being optically and/or thermally switchable, based on thermal or photochemical double-bond shifts (DBS) as well as methods for their preparation.

BACKGROUND OF THE INVENTION

Molecular and supramolecular devices e.g. molecular switches, photo-sensible complexants or molecular wires are currently of utmost interest, because they provide a novel approach for performing a variety of different tasks, like for instance photo-induced ion transport, photo-induced catalysis or electron transport within molecular wires. Basically, the function performed by a molecular or supramolecular device results from elementary properties performed by the components, such as photoactive, electroactive or ionoactive components, depending on whether they could operate with photons, electrons or ions. When it comes to photo-active molecular devices, usually a photo-sensitive component, like a disulfide bridge ((R—S—S—R') or an azo-component (R—N=N—R') within the underlying photo-sensitive molecule is involved. Upon irradiation with light of an appropriate wave-length, a cis/trans isomerisation can be induced within the photo-sensitive molecule, thus leading for instance to markedly different complexing properties of the entire molecule. As a result, complexation and transport of suitable guests (e.g. ions) can be performed and stopped under the influence of light. Examples of known molecular and supramolecular devices, e.g. photo-induced ion transport systems are described in F. Vögtle, Supra-moleculare Chemie, Teubner Studienbücher, Stuttgart 1992.

Another field of interest in connection with supramolecular or molecular devices is related to data processing by means of optical computing. Usual data processing is essentially performed with magnetic layers and/or digital electronic computers consisting of a large collection of interconnected switches, gates and memory elements called "flip-flops". Logic operations are performed by controlling the flow of electrons between these various components. Optical computers also use switches, gates and flip-flops in their logic operations, but the design of these devices are very different. The purpose of a switch is to make or break a connection between one or more transmission paths. If a switch controls the connection from just one path to another path, it is called a 1×1 switch. Other possibilities include 2×2, n×n, n×m switches whereby n and m could be any integer.

In optical computers, switches can be built from modulators using opto-mechanical, electro-optic, acusto-optic, magnetic-optic and other techniques. A well-known example represents the Mach-Zehnder interferometer in which the refractive index of one leg is electro-optically controlled and which is used as a 1×1 optical switch. By modulating the relative phase of the divided wavefronts as they pass through the interferometer, they can be constructively or destructively recombined at the output, thus creating an on-state or an off-state.

Another known optical switching design is the directional coupler which represents a 2×2 switch. Again, the electro-optic control of the refractive index of these devices shifts them between two states: cross and bar. Further modulators are known, whereby the on/off state is provided by liquid crystals or acousto-optic switches.

The above described optical switches are electrically or magnetically controlled. With the help of certain non-linear optical effects, all optical switches can be constructed as well. For example, by using the optical Kerr effect, it is possible to transform the above mentioned Mach-Zehnder interferometer into an all-optical switch.

Another feature of data processing is data storage by optical disks and holograms. The information on optical disks (e.g. CD-disks) is stored on the underside of said disk in a digital form represented by pits of different lengths embedded in an aluminum-coated layer protected by a surface coating of plastic. To read the information off the spinning disk, CW-light from a low power diode laser is tightly focused onto the pits by a short-focal-length objective mounted on a movable read head. Thus, the information stored by a binary code consisting of pits of different lengths can be repeatedly read-out.

An intense search for novel materials is currently under way, whereby said materials are intended to provide the possibility for information storage and processing. The underlying material must be modifiable by an external source so to apply an erasable or durable distribution of physical properties that could be determined by appropriate technical means for read-out purposes. Said physical properties could comprise among others optical properties, e.g. the refraction index, magnetic properties or mechanical properties like the different length of pits (e.g. in CD-disks).

One aspect of the present invention was to provide a novel material, i.e. novel chemical compounds, which displays two different states that can be determined for read-out purposes.

A further aspect of the present invention was to provide a method of information storage and data processing using said novel chemical compounds.

Still a further aspect of this invention was to provide novel photo-sensitive (4n)-annulene systems that are capable of thermal or photochemical double-bond shifts thus providing the possibility of switch from one conjugation state to another under the influence of an external source, e.g. light or heat.

Another further aspect of the present invention was to provide a method for preparing novel (4n)-annulenes that are capable of thermal or photochemical double-bond shifts.

DESCRIPTION OF THE PRIOR ART

It is well established that [4n]-annulenes such as heptalenes (n=3) or cyclooctatetraenes (n=2) appear, when suitably substituted, in constitutional isomers depending on the position of their C=C bonds at the [4n]-perimeter. The reversible interconversion of said double-bond shifted (DBS) isomers represents π-skeletal rearrangement that may be induced thermally or photochemically. The energy barriers separating the twisted double-boat forms of the two DBS isomers of heptalenes and tub forms of the two DBS isomers of cyclooctatetraenes, are mainly dependent on the number and bulkiness of contiguous substituents at the two annulenes, whereby, in the case of heptalenes, the size and number of the peri-substituents are specially relevant. Two typical examples are shown on scheme 1:

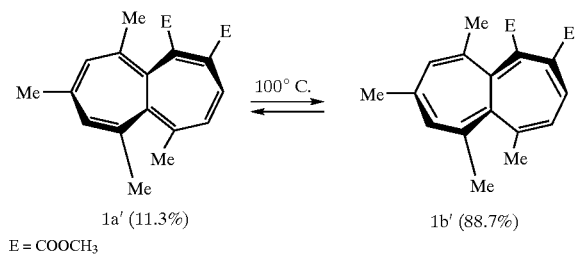

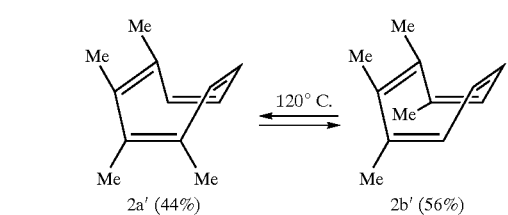

Nothing is known about the physical mechanism of the photochemical DBS process in heptalenes and cyclooctatetraenes. Nevertheless, it is known that the photochemical transformation of (−)-(P)-1b' leads to (−)-(P)-1a' without any loss of optical purity. This indicates that the excited state pathway must possess a similar topology as its ground state counterpart.

The thermal DBS process in heptalenes is, in general, not competed by other thermal reaction. The thermal racemization of optically active heptalenes possess distinctly higher $E_a$ values (e.g. (29.1±0.4) kcal mol$^{-1}$ ($\Delta G_{298}$=(31.8±0.6) kcal mol$^{-1}$)) for (−)-(P)-1a'→(MP)-1a'/1b') as compared with the corresponding DBS process. At higher temperatures (≧200°) heptalene-1,2-dicarboxylates may suffer a σ-skeletal rearrangement into heptalene-1,3-dicarboxylates and may also disintegrate to azulene-dicarboxylates. In contrast to heptalenes, cyclooctatetraenes, according to the $D_{2d}$ symmetry of their [4n]-core, are not inherently chiral, but may appear in antipodes due to their substitution pattern. The $E_a$ values of the racemization of optically active cyclooctatetraenes, which correspond to a net inversion of their tub form, are normally smaller than those for the DBS process or may become quite similar for both envisaged reactions. As a further thermal process that may interfere with the two discussed reactions a reversible disrotatory ring closure of cyclooctatetraenes can take place to yield bicyclo [4.2.0]-octatriene derivatives (e.g. 2a' is at room temperature in thermal equilibrium with a small amount of its bicyclic valence isomer, namely 1,2,7,8-tetramethylbicyclo-[4.2.0]-octa-2,4,7-triene. Nevertheless, in both systems, the DBS process can clearly be observed separately from the other thermal reactions. In addition, heptalenes offer the advantage that the DBS process takes place here with the lowest activation energy and only low energy irradiations (λ>360 nm) are necessary for the photochemical variant of the DBS process.

The different optical properties (e.g. UV/Vis-absorption) of the different valence isomers are also known.

In One photo- and thermochromic system based on cyclic double-bond shifts in heptalenes was, in principle, described by H.-J. Hansen in Chimia 50, (1996), No 7/8, page 341. However, said document does not provide sufficient information on the synthesis of such compounds nor does it provide any information on the possibility to exploit for data processing the fact that different physical properties (UV/Vis absorption) arises from the double bond shifts.

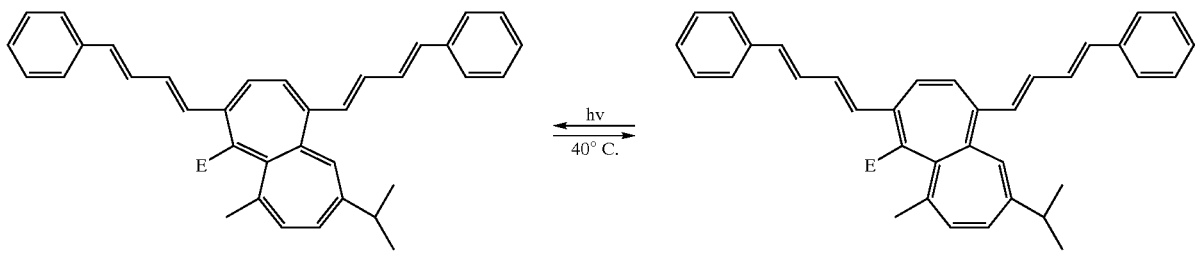

A BRIEF DESCRIPTION OF THE DRAWINGS

Figure 1B:
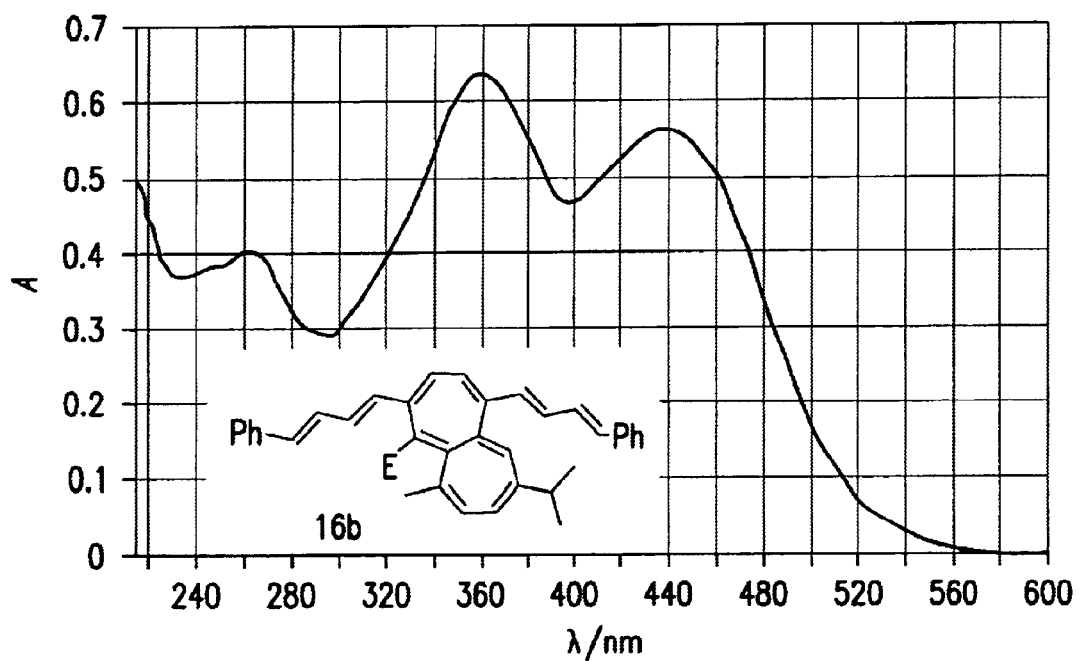

FIGS. 1A and 1B are UV/VIS spectra of 16a and 16b.
FIGS. 1B and 2B are UV/VIS spectra of 21a and 21b.

DETAILED DESCRIPTION OF THE INVENTION

The chemical compounds according to the present invention being optically and/or thermally switchable, due to thermal or photochemical double-bond shifts (DBS), usable for data processing, are comprising substituted [4n]-annulenes. An example of a [4n]-annulene is cyclooctatetraene (n=2). Preferred [4n]-annulenes are bicyclic [4n]-annulenes, i.e. fused [4n]-annulene systems, like heptalene.

An important feature of the inventive [4n]-annulenes is the fact that they comprise at least one substituent displaying an extended conjugated π-electron system which is in conjugation with the π-electron system of the [4n]-annulene core.

Particularly preferred are [4n]-annulenes wherein the perimeter substituents having an extended and conjugated π-electron system are located in 1,2- or 1,4-position of the annulene core. The basic principle is depicted in the following scheme 2:

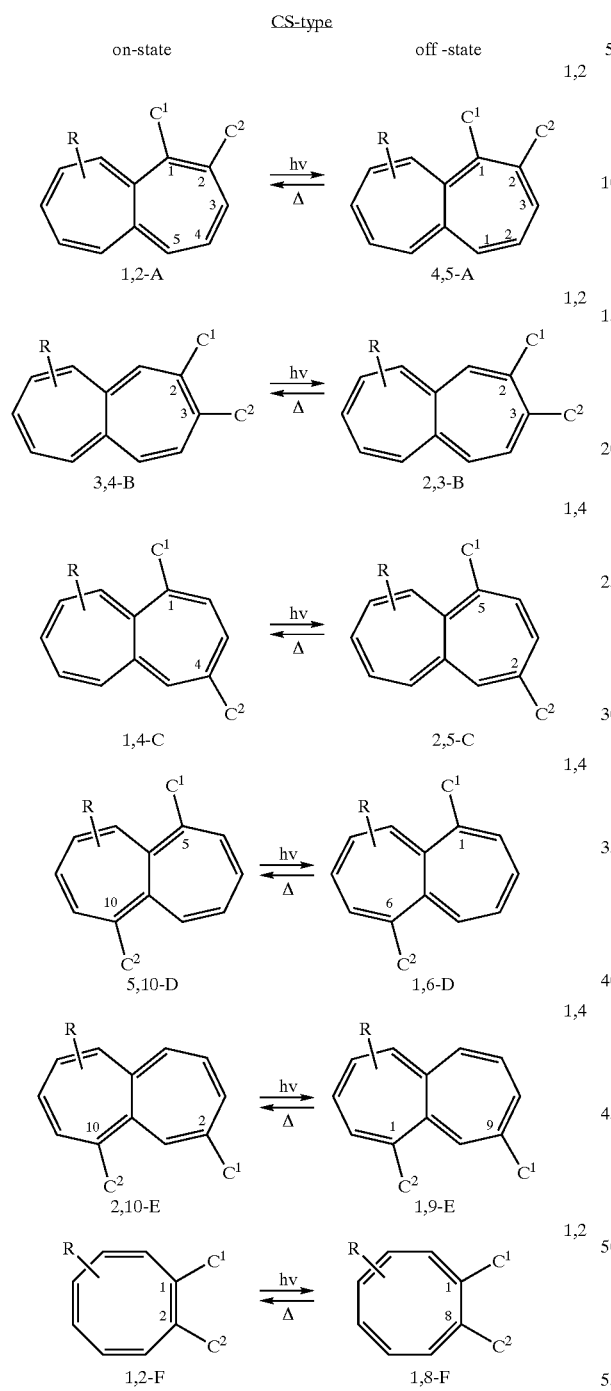

1,2-A     4,5-A     1,2
3,4-B     2,3-B     1,4
1,4-C     2,5-C     1,4
5,10-D     1,6-D     1,4
2,10-E     1,9-E     1,2
1,2-F     1,8-F $C^1$ and $C^2$ represent π-substituents which are capable of conjugation, whereas R represents non-conjugative substituents (e.g. alkyl groups) that could moderate via their steric interactions the activation energy of the thermal DBS process. The term CS denotes the conjugative switch in local 1,2- (1,2-CS) or 1,4-relation (1,4-CS) at the [4n]-perimeter. The on-state condition means that the substituents $C^1$ and $C^2$ are in conjugation via the ethylene or s-cis-buta-1,3-diene substructure of the [4n]-annulene core. The off-state condition means an interruption of the direct conjugation of the substituents $C^1$ and $C^2$.

A specific example illustrating two distinct conjugation states (on-state, off-state) caused by the photo-induced or thermo-induced double bond shift (DBS) is illustrated for heptalene whereby the group containing an extended conjugated π-electron system is a phenyl. group:

Scheme 3

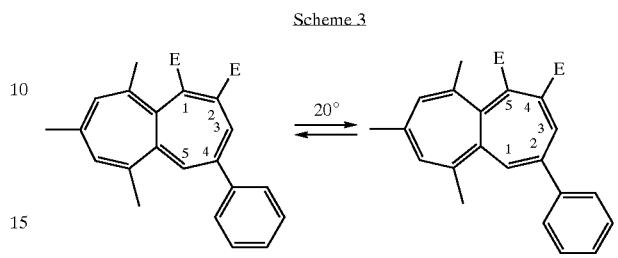

7a' (23%)        7b' (77%)

As can be seen from said formulas 7a' and 7b', the two distinct conjugation states differ in their π-electron conjugation of the π-system of the heptalene core with the substituent π-system, in as far as the conjugation of the phenyl π-electrons are better in a s-trans-cis-1,3-diene-conjugation with the π-system of the heptalene core 7a' along the annulene ring atoms $C_1$ to $C_4$, whereas in 7b' said butadiene conjugation along the annulene ring atoms $C_1$ to $C_4$ there is not a s-cis-buta-1,3-diene-conjugation, but only the less favorable $C_3$–$C_4$-atom allyl conjugation, respectively a $C_1$–$C_2$-atom vinyl conjugation.

The corresponding thermal and photochemical DBS process can be utilized as a molecular conjugative switch (CS) to bring on- or off-conjugation between π-substituents ($C^1$, $C^2$), placed in 1,2 or 1,4 relation at the [4n]-annulene core. Most obvious are the possible 1,2-CS systems. However, they have the disadvantage that the $C^1$ and $C^2$ substituents are close together in the on-state, which may lead to steric interactions between $C^1$ and $C^2$, thereby forcing one or both π-substituents out of conjugation. The 1,4-CS systems are more preferred, 1,4-C⇌2,5-C where conjugation between $C^1$ and $C^2$ can be realized via an s-cis-butadiene substructure. The torsion angles of such s-cis-butadiene substructures in heptalenes, carrying three or four peri-substituents (one being MeOCO, the others Me), vary in the narrow range of 33–34.5° and the $c_2$-symmetric 1,3,5,6,8,10-hexamethyl-heptalene may be taken as a model compound.

Scheme 4

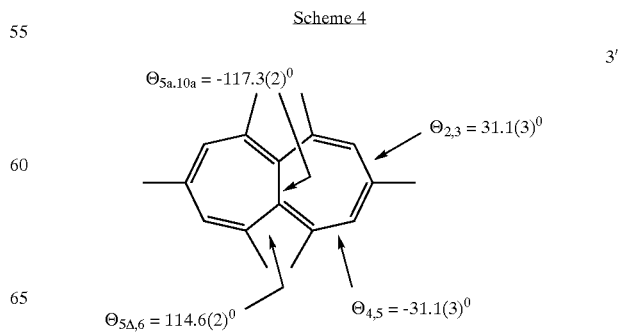

$\Theta_{5a,10a} = -117.3(2)^0$
$\Theta_{2,3} = 31.1(3)^0$
$\Theta_{5A,6} = 114.6(2)^0$
$\Theta_{4,5} = -31.1(3)^0$ -continued

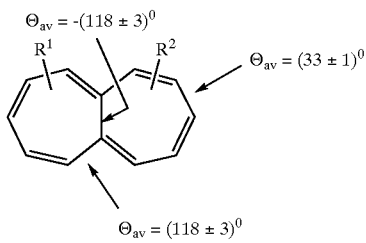

4'

This means that conjugation via the s-cis-butadiene subunits is not reduced by more than a fifth, assuming that $C^1$ and $C^2$ are in an optimal conformation (i.e. θ near 0 or 180°) with respect to "their" heptalene double bonds in the on-state. The systematically possible 1,4-CS arrangement 5,10-D⇌1,6-D and 2,10-E⇌1,9-E are less effective as conjugative switches due to the unfavorable $\theta_{av}$ of the involved s-trans-butadiene subunits which vary in the range of 114–124° (D-type) and 118–127° (E-type) for heptalenes bearing three or four peri-substituents (see scheme 4) and will reduce conjugation by up to 60%. The situation is similar to higher substituted cyclooctatetraenes where X-ray crystal diffraction analyses reveal that the average torsion angles between the ethylene subunits fluctuate in the range of 64 to 69°. Therefore, cyclooctatetraenes are only useful as switches in the 1,2-CS setting.

The transition state of the DBS process in heptalenes is non-planar with a maximum symmetry of $D_2$ of the heptalene core as it is demonstrated by the isoconfigurational transformation of optically active heptalenes. π-SCF-force field calculations by Lindner and Flöter are in agreement with these findings.

The above mentioned publication of H.-J. Hansen does disclose photo- and thermochromic systems based on cyclic double bond shifts in heptalene together with UV/VIS spectra. Said document discloses that the π electron system of the substituent is brought during the shift from a s-cis to an s-trans state and vice versa. However, it was now found that the heptalenes undergo said valence isomerisation (DBS) via a non-planar transition state while maintaining their overall stereochemical configuration (see also the above discussion). As a result, the on-state DBS-isomer, wherein the perimeter substituent displaying an extended π-electron systems being in s-trans position relative to the core butadiene π-electron system, is not switched to a corresponding off-state DBS-isomer wherein said perimeter substituent displaying an extended π-electron system is in s-cis position relative to the core butadiene π-electron system, but remains in an s-trans position.

FIGS. 1A and 1B provide an example of such a UV/VIS spectra of the two DBS-isomers 16a, respresenting the off-state of this 1,4-CS system and 16b being equivalent with the on-state. The [4n]-annulene in FIGS. 1A and 1B is a heptalene, having two substituents that display an extended π-electron system. Said substituents are both a phenyl-trans-butadiene group that are in 1,4-relation to each other. The three main heptalene bands of said FIG. 1A are clearly recognizable in the spectrum of 16a. Band I appears as a weak shoulder at ca. 430 nm, followed by the much more intense shoulder of the band II at ca. 375 nm which is just recognizable at the long-wavelength flank of band III. The latter one, appearing at 345 nm, represents the dominating absorption band in the spectrum of 16a. The switch to the on-state is quite impressive. The spectrum of 16b shows now an immense absorption band at 443 nm, perhaps due to the superposition of the heptalene bands I and II. The heptalene band III is clearly separated and appears at 360 nm, i.e., bathochromically shifted by 15 nm as compared to the off-state spectrum.

The two states of the 1,4-CS system 16a⇌16b can also be recognized with the bare eye. When an orange-colored hexane solution of the thermal equilibrium mixture of 16a and 16b is irradiated at ca. 0° with (439±10) nm-light in a vessel and is kept in the dark in a second vessel only the solution in the irradiated vessel turns to pure yellow which is clearly distinguishable from the still orange color of the protected solution.

It is important to state that the above outlined different conjugation states, being the result of double-bond shifts (DBS) resulting in different UV/VIS spectra of the DBS isomers of [4n]-annulenes, provide the possibility to use said two distinct conjugation states (conjugation on-state and conjugation off-state) for information storage and processing purposes. This is due to the fact that with the help of external stimuli, like heat and/or light of an appropriate wave-length, the conjugation on-state can be switched to a conjugation off-state and vice versa, and furthermore, to the fact that the substitution pattern on the heptalene system can be tailored to provide a desired thermal activation barrier. Systems being stable in solution in respect of DBS up to temperatures of up to 150° C., like for instance dimethyl 4,5,6,8,10-pentamethylheptalene-1,2-dicarboxylate having further π-substituents are provided by the present invention in the same way as the system 7a/7b (see scheme 3) interconverting readily at a temperature of about 20° C. With thermal interconversion, the equilibrium mixture is determined by the relative stability of the two DBS forms, with the on-state form being frequently, but not always, the more stable form.

The situation is entirely different for photochemical DBS-interconversion, wherein the equilibrium mixture depends on the relative extinction coefficients of the on-state and off-state. Thus, irradiation at longer wavelengths, where the on-state displays a higher extinction coefficient, depletes this state and populates the off-state, while irradiation at shorter wavelengths, where both states have more similar extinction coefficients, leads basically to an entirely different equilibrium mixture.

In the solid state the situation is quite different, i.e. no conjugation state switching is taking place. This is because in the solid state there is insufficient local mobility of the [4n]-annulene molecules, e.g. the heptalene moiety, so that said molecules are prevented from performing the isomerisation process implying the $C_2 \rightarrow D_2$ conformational transition. Consequently, this provides a way for gating the photochemical DBS interconversion. In a preferred embodiment of the present invention, appropriately substituted heptalene molecules are embedded in a suitable carrier matrix which remains locally rigid up to a desired temperature. Said carrier matrix can comprise a low-melting glass or polycarbonates, polyacetates, polymethacrylates, polystyrenes and copolymers thereof, as well as copolymers with a polymerisable [4n]-annulene.

In such copolymers with a polymerisable [4n]-annulene as one monomer, at least one of the groups E (see scheme 1) has to be a group —COO—$(CH_2)_n$OH for polycarbonates (n≧2), a group —COO—$(CH_2)_n$OOC—C($CH_3$)=$CH_2$ for methacrylates (n≧2), a group —COO—$(CH_2)_n C_6 H_4$-4-CH=$CH_2$ for polystyrenes (n≧2).

Even in the presence of appropriate light, preferably of a wavelength being in the range of 360 to 600 nm, no photo-induced conjugation switching occurs, unless the local mobility of the heptalene moiety is restituted by softening of the matrix, either by global warming or by local heating with sufficient intensity, preferably by a red or near IR-laser.

Thus, for data processing purposes, e.g. in order to store data on heptalene containing material in a sequential manner, a binary code can be set-up and which is consisting in the conjugation on-state and the conjugation off-state. In order to switch from the conjugation on-state to the corresponding conjugation off-state via double bond shift and to freeze the locally generated conjugation state, the [4n]-annulene (e.g. heptalene) molecules are embedded in said polymer matrix, the desired data is applied by means of a suitable low-energy, diode laser of a distinct wavelength, while simultaneous irradiation with photochemically active light takes place, if required, whereby locally the conditions are created for the double bond shift entailing the switch from the conjugation on-state to the conjugation off-state and once the laser moves to the next (neighboring) place, upon cooling down, the thus generated conjugation switch is, as matter of fact, freezed in the solid state, so that no reverse switching from the conjugation off-state to conjugation on-state is possible any more. Consequently, unlike conventional compact disks, where the information is stored on the underside of said disk in a digital form represented by pits of different length, the present invention provides a data storage material based on locally defined conjugation states, thus generating a binary code, like conventional CDs.

If no carrier matrix is employed for performing the DBS, a low melting [4n]-annulene has to be used. The photo-induced double-bond shift (DBS) has to be performed after prior softening of said solid [4n]-annulenes (e.g. in crystalline form) so that the mobility of said [4n]-annulene, e.g. heptalene, is increased. In a semi-molten state or in a molten state, said [4n]-annulenes do undergo said photo-induced double-bond shift (DBS). In this context it is important to mention that the [4n]-annulene selected for data storage, irrespective of the presence of a carrier matrix or not, must remain chemically stable upon heating, i.e. only those [4n]-annulenes are to be selected for these purposes that do not undergo a chemical decomposition reaction.

Still another possibility of data storage is the generation of a matrix comprising tiny liquid drops containing the solubilized [4n]-annulenes and which are embedded in a solid matrix. Such a drops-containing matrix provides the possibility of the application of distinguishing signs upon all kinds of documents, bank-notes or credit cartes. Depending on what kind of [4n]-annulene, e.g. heptalene, is chosen, the distinguishing sign comprising said [4n]-annulene, e.g. heptalene, according to the present invention is bleached upon exposition to an appropriate light, due to the switching from the conjugation on-state being colored to the conjugation off-state being bleached. The reverse switch then takes place automatically upon exposing said sign to the normal ambient light, where the natural equilibrium is re-adjusted. Thus, the change of color upon exposition to light provides a non-falsifiable, non-copyiable distinguishing sign for said documents.

Still another possibility is the use of the heptalene plus matrix system as a gatable (vide supra) photochromic material for holographic storage. An object and a reference, beam of a photochemically active wavelength are brought to interference in a cube or thick layer of a glass or polymer, containing a suitable [4n]-annulene, e.g. a heptalene, kept at a temperature sufficient to permit the generation of a photochemically generated holographic interference pattern. After lowering the temperature, the hologram, thus generated, becomes insensitive to light and can be read-out in the usual manner. Conversely, a thermal holographic interference pattern can be generated by a pulsed object and reference beam in a heptalene plus matrix system which either contains, at the outset, a distribution of on states and off-states being not in thermal, or which is irradiated simultaneously under light of a photochemically active wavelength.

According to the present invention, a multitude of [4n]-annulene molecules are arranged in a 1-dimensional, or 2-dimensional or 3-dimensional way wherein said conjugation states are spacially non-uniformly modulated. This means that the switchability of $\pi$-electrons within the [4n]-annulene system giving rise to two distinct conjugation states via double bond shifts is used for information (data) storage or processing purposes. Thereby, it is necessary to provide a carrier system, like a film, a disk or a cube that allows the modulation of a multitude of the corresponding [4n]-annulene molecules for the permanent, or erasable, storage of their corresponding conjugative state. Thus, upon modulating said conjugation states, a defined distribution thereof is generated upon said carrier that corresponds to the information that is intended to be stored. Conveniently, the matrix described above simultaneously serves as such a carrier.

Further to said step of modulating a multitude of [4n]-annulene molecules in a 1-dimensional or 2-dimensional or 3-dimensional way and wherein said conjugation states are spacially non-uniformly modulated, a further step is performed wherein at least one of the optical, electric or magnetic properties being attributable to said conjugation states is determined and processed. Examples for optical properties are light absorption and emission, the index of refraction, non-linear responses, chiro-optical properties (in chiral systems). Also the response of optical properties to external influences can be harnessed, e.g. applied electrical/magnetic fields, stress. As an example, the "Kerr-effect", which is well known to the man of the art, is to be mentioned in this respect. Examples for magnetic and/or electric properties are electrical conductivity (conducting polymer with inserted [4n]-annulene molecules) and magnetic susceptibility.

Any means known in the art can be used so that said conjugation states of the [4n]-annulenes are determined by a suitable read-out step. Preferably said read-out step is an optical read-out step.

Possible applications of devices making use of the switchability of double-bond shifts related conjugation states comprise among others optical recording materials, i.e. means for the optical recording of information, or means for the optical switching and computing, or optically switched photoconductive polymers. This could be realized by combining the optical switchability of the [4n]-annulenes, notably the heptalenes according to the present invention, with molecular wires, like caroviologen thus affording optically switchable molecular wires.

In a preferred embodiment for said application, a multitude of [4n]-annulene molecules are arranged in a 2-dimensional way whereby said conjugation states are spacially non-uniformly modulated. Thus a conformationally restricted matrix system is generated by modulating said conjugation states. An example for an optical recording material is a compact disk (CD): Conventional recordable CD's are classified as either write-once-read many, or erasable. Write-once optical storage, commonly called writeonce-read-many (WORM), is designed for archival data storage applications, especially those that require an indelible trail, such as birth, medical and insurance records. Consequently, WORM disks are constructed with permanence and storage capacity in mind. Upon embedding suitable [4n]-annulenes within a polymer matrix, thus being in a solid state, they could provide both possibilities of write-once as well as erasable data storage systems, depending on the method that is provided for permanently storing said data. For write-once-read-many compact disks this would depend on whether a conformationally restricted matrix system is employed for embedding said [4n]-annulenes, or on whether the recording is performed by purely thermal means by e.g. coloring a bleached film pit by pit by means of a small IR-laser. Still another alternative to provide a WORM-CD would be to record through bleaching by application of IR laser, in order to melt the polymer matrix locally while the film is irradiated with blue light.

Erasable and fully rewritable optical disks (CD) can be easily obtained by locally exposing the matrix containing the [4n]-annulene molecules to a suitable laser, thus softening slightly the polymer matrix which provides the condition for the switchability between said conjugation states and whereby a suitable wavelength is opted for making sure that said conjugation switch is actually taking place.

A further preferred embodiment of data processing by means of [4n]-annulene molecules consists in arranging a multitude of [4n]-annulene molecules in a 3-dimensional way whereby said conjugation states are spacially non-uniformly modulated, thus generating a holographic grating by modulating said conjugation states. Thus, further to the 2-dimensional modulation, there is the 3-dimensional modulation of [4n]-annulene molecules for data processing for the commonly called holographic memory, or, conversely, a holographic correlator.

A further possibility is the optical computing, where the spatial light modulator frequently found in programmable parallel processing arrangements is based on a film containing the [4n]-annulenes, preferably the heptalenes, according to the present invention. The pixel pattern in such a film is defined by the [4n]-annulene, preferably heptalene, molecules being either in the conjugation on-state or conjugation off-state. The pattern is imprinted by a beam of visible or near IR-light which passes through said film, either as a spatial intensity variation or a spatial variation of the phase of the electromagnetic radiation. Switching of the pattern is accomplished by switching the distribution of conjugation on-states and conjugation off-states of the the substituted [4n]-annulenes, preferably substituted heptalenes, molecules by any of the methods outlined in the preceeding sections dealing with data storage. One can either irradiate the film with a large area beam of appropriate wavelength and with the desired spatial intensity distribution, or by rapidly scanning the surface with an appropriately modulated write-beam focused on the desired pixel dimension. Furthermore, a holographic pattern can be set-up in a film of appropriate thickness or in a volume containing [4n]-annulene, preferably heptalene, molecules by bringing to interference a reference and an object beam in said volume. Such a hologram is of a lasting or transitory nature depending on the choice of the substituted [4n]-annulene, preferably substituted heptalene system according to the present invention. The absorption pattern, or the index of refraction pattern, associated with such a hologram, can be used for the parallel routing and distribution of information carrying light. This latter term is always meant to include near and near IR-radiation. A further function which is performed by a system containing the substituted [4n]-annulenes, preferably substituted heptalenes according to the present invention, due to its light by light modulating capacity, is that of a fully optical flip-flop. In this case, a preferred system is a liquid film containing substituted [4n]-annulene, preferably substituted heptalene, molecules with the conjugation on-state being thermally more stable than the conjugation off-state, but with rapid interconversion of the two states at the chosen temperature. For a beam of light with a wavelength falling into the region where the on-state system primarily absorbs, the film becomes bleached in proportion to the intensity of the incident beam. Thus, the amount of the transmitted light is a non-linear function of the amount of the incident light, and by feeding back a part of the transmitted light into the beam of the incident light, an optical flip-flop with an opaque and bleached state is realized. The system is similar to an optical saturable absorber with two crucial advantages: bleaching can be essentially complete (saturable absorber: max 50%) and the lifetime of the bleached state is determined by a thermally controllable interconversion rate between for instance the [4n]-annulene, preferably heptalene, conjugation on-state and conjugation off-state, and not by the radiative lifetime of the electronically excited state. Thus, systems working with low light levels can be designed by means of the [4n]-annulene, preferably heptalene, molecules according to the present invention.

Still another possibility for application is a material comprising basically two components, whereby one component provides the two conjugation states (on-state and off-state) having different optical properties and which consists of the inventive substituted [4n]-annulenes. The second component comprises preferably a system that is performing a distinct function, e.g. electron transport, complexation or catalysis, but which depends on the switchable optical responses of the first component. As a result a supramolecular system can be set-up, whereby one component is switching the conductive, complexing or catalytical activities of the second component.

The two-component system could also be realized in one substituted [4n]-annulene system only. As was already pointed out, those contiguous substituents within the [4n]-annulene system which do not provide π-conjugation (e.g. alkyl groups) are to be adjusted in a way that they provide the desired sterical configuration for the optimal conformational switch. Hence, by providing further photosensitive contiguous substituents, e.g. in the positions 7, 8 or 9 of the heptalene core, the conformational switch can be influenced by a first wavelength, whereas the double bond shift is performed by a second wavelength. For instance, by using a heptalene perimeter substituent carrying an azo-group, like azobenzene, being susceptible to cis/trans isomerisation under light of $\lambda$ being at about 320 nm, thus affording two conformational situations for the entire heptalene system, the double-bond shifts could be triggered by means of a second light source of $\lambda$ being at about 430 nm, instead of using heat to provide conformational mobility. Thereby it is important that said photosensitive contiguous substituents are selected and adjusted in a way that one of said two conformational situations within said perimeter substituent allows the double-bond shifts of the heptalene, whereas the other does not. This embodiment can be employed in cases where the required heating to increase the conformational mobility of said heptalenes is not practicable, for instance because the annulenes are not stable under the given thermal circumstances, or higher speed or lower energy input is desirable.

Further to the aspect of data storage by using materials containing the inventive substituted [4n]-annulenes and the method to employ said conjugation on-state and off-state in order to establish a binary code onto a data carrying system, the present invention also provides a method to read out said data. As was extensively pointed out said two conjugation states provide distinguishable physical properties. Notably optical properties, like the index of refraction or the absorption of both conjugative states can be used for read-out purposes.

In a preferred embodiment, for instance a IR-laser is used for scanning the surface of a disk, whereupon the data is recorded or stored like on a conventional disk, and a further means detecting and processing the difference in refraction or absorption of the spatially non-uniformly modulated conjugation states provides the actual data processing. Thus, the spacially non-uniformly modulated conjugation states can be used for optical recording of information or for optical switching and computing, as well as light modulating purposes.

Preferred substituted [4n]-annulenes are [4n]-heptalenes of the following formula (I) or (II) having at least one substituent with an extended π-system

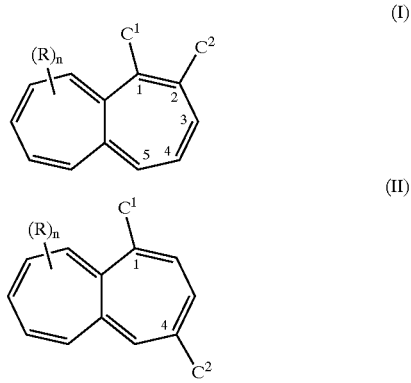

whereby $C^1$ and $C^2$ represent independently from each other a hydrogen atom, a substituted or unsubstituted $C_1$–$C_{12}$-alkyl group, a substituted or unsubstituted $C_1$–$C_{12}$-alkoxy group, a substituted or unsubstituted aryl-$C_1$–$C_{12}$-alkyl group, a substituted or unsubstituted $C_1$–$C_{12}$-alkenyl group, a substituted or unsubstituted $C_1$–$C_{12}$-conjugated alkenyl group, a substituted or unsubstituted $C_1$–$C_{12}$-alkinyl group, a substituted or an unsubstituted phenyl group, a substituted or an unsubstituted heterocyclic group, a cyano group, a nitro group, a thiocyanate group, a $C_1$–$C_{12}$-ester group being optionally polymerisable with copolymers, with the proviso that at least one of said substituents $C^1$ and $C^2$ contains a π-electron system which is in conjugation with the π-electron system of the heptalene core, and whereby said [4n]-heptalenes can comprise at least one further substituent R being selected from the above indicated groups with n being 0–8, provided that if one of the at least one further substituents R is a isopropyl group at the position 9 of the heptalene ring, the substituent at the position 6 must not be a methyl group.

In a preferred embodiment of the present invention, said further substituents are selected from the group comprising substituted or unsubstituted $C_1$–$C_{12}$-alkyl groups or photoactive diazo-containing groups, like azobenzen. Said further substituents are preferred in order to provide for the conformational switchability of the annulene, i.e. in order to adjust the activation barrier for said conformational switchability.

In case that the [4n]-heptalenes are forming a carrier matrix together with further copolymers, they preferably contain polymerisable substituents. In such copolymers with a polymerisable [4n]-annulene, e.g. a heptalene, as one monomer, at least one of the groups $C^1$, $C^2$ or R has to be a group —COO—$(CH_2)_n$OH for polycarbonates (n≧2), a group —COO—$(CH_2)_n$OOC—$C(CH_3)$=$CH_2$ for methacrylates (n≧2), a group —COO—$(CH_2)_nC_6H_4$-4-CH=$CH_2$ for polystyrenes (n≧2).

Particularly preferred [4n]-heptalenes $C^1$ and $C^2$ represent independently from each other a hydrogen atom, a methyl group, a phenyl group, an ethyl ester group, a methyl ester group, a (E)-PhCH=CH group, a (E)-4-MeOC$_6$H$_4$CH=CH group, a (E)-4-ClC$_6$H$_4$CH=CH group, 4-MeOC$_6$H$_4$ group, a —CH=CH—CH=CH—C$_6$H$_5$ group, a —CH=CH—C$_6$H$_4$NO$_2$-4 group, a —CH=CH—C$_6$H$_4$OMe-4 group.

Particularly preferred heptalenes are those which carry extended π-substituents on the positions 1 and 4, notably π-substituents carrying themselves donor-acceptor groups, e.g. a butadienyl-4-(p-nitrophenyl) substituent, or a butadienyl-4-(p-methoxyphenyl) substituent, or alternatively one donor-substituted π-substituent in the position 1 and and acceptor-substituted π-substituent in the position 4. Thus, two markedly different conjugation states with pronounced photochromic properties can be obtained. In order to adjust the desired temperature for the double-bond shifts to take place, it is preferable to adjust the further substituents around the heptalene core. This is in order to influence the mobility of the [4n]-annulene molecules, e.g. the heptalene moiety, so that said molecules are prevented from performing too readily (i.e. on low temperatures) the isomerisation process implying the $C_2 \rightarrow D_2$ conformational transition. In order to realize high temperatures for the double-bond shifts to take place, the conformational switchability has therefore to be restricted. This can be realized by adding further $C_1$–$C_{12}$-alkyl groups. For instance, through multiple methyl substituents on the positions 6–10, preferably with a methyl group on each of said positions, the conformational switchability can be substantially reduced, thus leading to high activation barriers for the transfer from one DBS-isomer to another.

A further aspect of the present invention is the preparation of novel heptalenes substituted with extended π-systems.

A preferred method for the preparation of substituted [4n]-heptalenes of the formula (I) or (II)

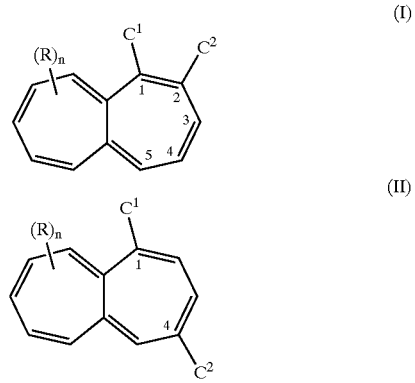

whereby $C^1$, $C^2$, R and n are as above defined, comprises the steps of a) obtaining a heptalenedicarboxylate by a reaction of a correspondingly substituted azulene with acetylenedicarboxylate, (b) transforming said methyl substituent at the position 1 of the heptalene ring into the desired conjugated substituent having an extended π-electron system, (c) optionally, transforming at least one of the carboxylate substituents into a further group displaying an extended π-system.

Preferably, a heptalene-4,5-dicarboxylate carrying a methyl substituent at the position 1 of the heptalene ring is obtained.

Heptalenedicarboxylates are readily available through Diels-Alder reaction of activated acetylenes with suitable azulenes. Thus, the introduction of an alkyl group around the heptalene core, preferably in 1 or 2-position is possible and furthermore 2 carboxylic acid or ester groups are also incorporated, preferably in 4 and 5-position. Although perimeter carboxylate substituents do already represent substituents that could be in conjugation with the π-electron system of the heptalene ring, it is preferred to transform at least one of said carboxylic groups into a substituent displaying an extended π-electron system, or to transform another group that was entered by the preliminary Diels-Alder reaction into a suitable substituent displaying an extended π-electron system. Thus, for instance the methyl group in position 1 being transformed into a substituent displaying an extended π-electron system, plus one carboxylic ester group, preferably in the 4-position, being also transformed into a substituent displaying an extended π-electron system provide a system wherein the butadiene subunit within the annulene core is in an extended conjugation with the π-substituents of the position 1 and 4.

In the following, the preparation of novel heptalenes according to the inventive method of preparation, their photochemical behavior as well as their application for data processing shall be illustrated, whereby it is to be stated that the following examples are not to be construed as being limiting the entire scope of the present invention.

EXAMPLE 1

Preparation of dimethyl 9-isopropyl-1,6-dimethylheptalene-4,5-dicarboxylate (2b) and its Corresponding Halogenation Products (4b and 5b)

Commercially available guaiazulene (10.0 g, 0.05 mol) and dimethyl acetylenedicarboxylate (ADM; 18.0 ml, 0.15 mol) are dissolved in toluene (150 ml) and heated in a closed vessel at 130° C./24 h. Toluene is distilled off and the residue dissolved in a minimum amount of Et$_2$O. At 4° C., 2b deposits in yellow crystals. The residue of the mother liquor is chromatographed on silica gel (hexane/Et$_2$O 4:1) to yield a second batch of 2b. In total, 11.6 g (68%) of pure 2b are obtained; m.p. 147° C.

Preparation of the bromide 4b: Reaction of 2b with a molar amount of NBS in boiling CCl$_4$ in the presence of a catalytic amount of (C$_6$H$_5$COO)$_2$ gives in 76% yield a 3:1 mixture of bromide 3b and 4b (see scheme 5). Only the excess bromide 3b could be obtained by crystallization from Et$_2$O in pure form. On heating, it decomposes before melting. Bromide 4b is found in the Et$_2$O mother liquor in enriched form.

Preparation of the chloride 5b: Heptalene 2b (7.2 g, 0.021 mol) and C$_2$Cl$_6$ (26 g, 0.11 mol) are dissolved in THF (190 ml) and the solution cooled to −78° C. (dry ice/acetone bath). A solution of t-BuOK (11.25 g, 0.10 mol) in THF (90 ml) is added slowly to the aforementioned solution under stirring and an atmosphere of N$_2$. The reaction mixture is stirred for additional 90 min at −78° C. and then poured into water. The organic layer is taken up in Et$_2$O and then 3 times washed with water and finally dried (Na$_2$SO$_4$). The solid residue of the Et$_2$O extracts is washed with hexane to remove excess C$_2$Cl$_6$. The residual orange-colored crystal powder is recrystallized from EtOH at 40° C. to yield pure 5b (7.0 g, 88%); m.p. 109.5–111.0° C.

Scheme 5

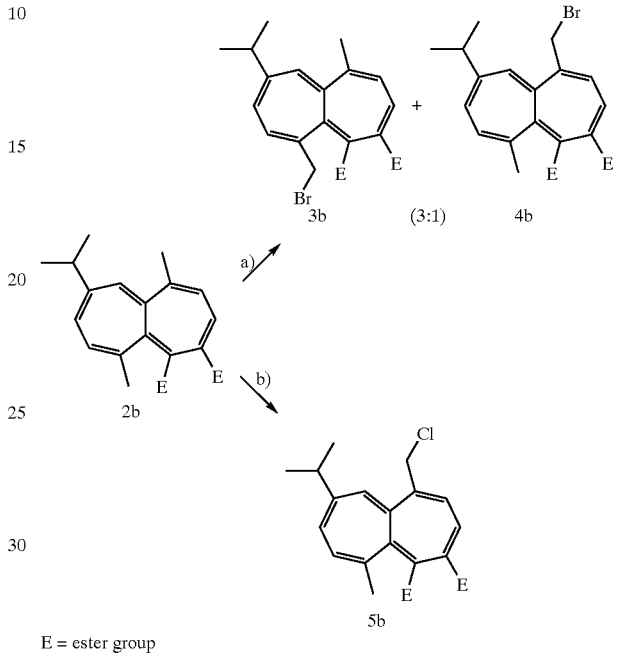

E = ester group

The established through-conjugation in 1-substituted heptalene-4,5-dicarboxylates is also effective chemically, i.e., it is expressed in a higher acidity of the H-atoms of the Me group at C(1) as compared to that of the H-atoms of the Me group at C(6) in 2b. Indeed, the reactivity differences of the two Me groups in 2b are striking. Whereas N-bromosuccinimide (NBS) in boiling CCl$_4$ leads mainly to the introduction of a Br-substituent at the 'olefinic' Me group at C(6), the reaction of 2b with t-BuOK in THF at −78° in the presence of hexachloroethane as electrophilic chlorinating agent gives exclusively, in excellent yields, the 5-chloro-methylheptalene 5b.

Irradiation of H—C(10) in 3b (s at 5.85 ppm; CDCl$_3$) induces a strong enhancement of the signal of Me—C(1) at 2.20 ppm, but no effect on the AB system of BrCH$_2$—C(6) at 4.25 and 4.03 ppm (J$_{gem}$=10.1 Hz). The opposite effects are observed when H—C(10) of 5b (s at 5.90 ppm; CDCl$_3$) was irradiated. In this case, the signals of the AB system of ClCH$_2$—C(1) at 4.21 and 4.15 ppm (J$_{gem}$=12.2 Hz) are strongly enhanced, in contrast to the signal of Me-C(6) at 2.04 ppm which remains unchanged The $^1$H-NMR spectrum (CDCl$_3$) of 4b is almost identical with that of 5b. The AB system of BrCH$_2$—C(1) appeared at 4.13 and 3.95 ppm (J$_{gem}$=12.5 Hz). The larger value for J$_{gem}$ of 4b as compared to 3b is in agreement with a strong 'through-conjugation' in the latter. None of the halogenated heptalenes 3b to 6b displays in its $^1$H-NMR spectra signals of the corresponding DBS isomers 3a to 6a.

EXAMPLE 2

Preparation of dimethyl 6,8,10-trimethyl-4-phenylheptalene-1,2- and dimethyl 6,8,10-trimethyl-2-phenylheptalene-4,5-dicarboxylate (7a' and 7b')

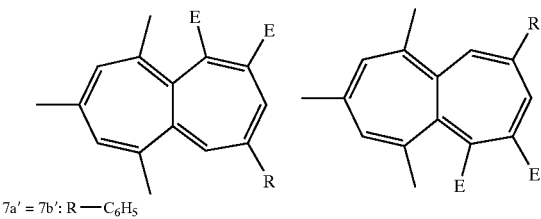

7a' = 7b': R—$C_6H_5$
E = ester group 4,6,8-Trimethyl-2-phenylazulene (0.292 g, 1.00 mmol) and dimethyl acetylenedicarboxylate (0.215 g; 1.50 mmol) are heated in decalin (4 ml) for 5 h at 190°. Further dimethyl acetylenedicarboxylate (0.215 g; 1.50 mmol) is added and the heating is continued for additional 3 hours until most of the azulene is consumed (TLC control). Thereafter, all volatile material is removed at 50°/HV and the residue subjected to a column chromatography on silica gel with hexane/$Et_2O$ (7:3) as eluant. Four fractions are obtained. The first fraction contained none-consumed azulene (0.030 g; 10%), the second fraction contained dimethyl (E)-1-(4,6,8-trimethyl-2-phenylazulen-1-yl)ethene-1,2-dicarboxylate ((E)-20') (0.015 g; 4%), the third one a 23:77 mixture of 7a'/7b' (0.140 g; 36%), and the last fraction contained dimethyl 4,6,8-trimethylazulene-1,2-dicarboxylate (0.034 g; 12%).

Data of (E)-20'. Brown needles, m.p. 147.5–148.50 ($Et_2O$/hexane). UV (MeOH): $\lambda_{max}$ 397 (4.19), 305 (4.95), 248 (4.65); IR ($CHCl_3$): 3030w, 2930m, 2860m, 1720s, 1600m, 1430m, 1260s, 1020m, 820m. $^1$H-NMR (300 MHz, $CDCl_3$): 7.36 (m, 5 arom. H and H—C(3)); 7.08 (s, MeOCCOCH═); 7.03 (s, H—C(5,7)); 3.74, 3.36 (2s, 2 MeOCO); 2.88 (s, Me-C(4)); 2.76 (s, Me-C(8)); 2.60 (s, Me-C(6)). CI-MS: 391 (7), 390 (23), 389 (100, [M+1]$^+$). EI-MS: 389 (23), 388 (100, M$^+$), 330 (21), 329 (98, [M−COOMe]$^+$), 328 (26), 298 (50), 297 (50, [M−COOMe−MeOH]$^+$), 271 (9), 270 (43, [M−2COOMe]$^+$), 269 (32).

Data of 7a': Thermal equilibrium amount at room temperature in the presence of 7b' is 23%. $^1$H-NMR (300 MHz, $CDCl_3$; in the presence of 77% of 7b'): 7.51–7.31 (m, 5 arom. H); 6.78 (s, H—C(3)); 6.12 (s, H—C(9)); 6.04 (s, H—C(5)); 5.96 (s, H—C(7); 3.86, 3.74 (2s, 2 MeOCO); 2.16 (s, Me-C(6)); 1.99 (s, Me-C(8)); 1.68 (s, Me-C(10)).

Data of 7b': This form crystallizes from the 77:23 equilibrium mixture with 7a' in $Et_2O$/hexane in orange crystals; m.p. 171.3–172.1°. IR (KBr): 2950w, 1720s, 1700s, 1640w, 1600w, 1570w, 1490w, 1440m, 1430s, 1390w, 1370w, 1330m, 1310m, 1280s, 1230s, 1200m, 1190m, 1130s, 1050m, 1040m, 1000w, 960w, 930w, 920w, 880w, 850w, 810w, 780m, 770m, 740m, 700m. $^1$H-NMR (300 MHz, $CDCl_3$, −20°): 7.88 (s, H—C(3)); 7.51–7.31 (m, 5 arom. H); 6.32 (s, H—C(1)); 6.19 (s, H—C(9)); 5.97 (s, H—C(7)); 3.75, 3.71 (2s, 2 MeOCO); 2.05 (s, Me-C(8)); 1.99 (s, Me-C(6)); 1.84 (s, Me-C(10)). $^1$H-NOE (400 MHz, $CDCl_3$): 1.84 (Me-C(10))→6.19 (s, H—C(9)), 6.32 (s, H—C(1)); 2.05 (Me-C(8))→6.19 (s, H—C(9)), 5.97 (s, H—C(7)). EI-MS: 389 (16), 388 (100, M$^+$), 373 (11), 341 (23), 329 (28, [M−COOMe]$^+$), 297 (11), 286 (12, [M−PhC≡—CH]$^+$), 269 (27), 255 (17), 254 (22), 253 (14), 252 (18), 247 (13), 246 (88, [M−E−C≡−C−E]$^+$). Anal. calc. for $C_{25}H_{24}O_4$ (388.47): C 77.30, H 6.23; found: C 77.09, H 6.43.

EXAMPLE 3

Preparation of dimethyl 1-(4-phenylbuta-1,3-dien-1-yl)heptalenedicarboxylate

Compound 5b (1.0 g, 2.66 mmol) of example 1, NaI (0.60 g, 4.0 mmol), and $PPh_3$ (1.4 g, 5.32 mmol) are dissolved in acetone (6.5 ml) and the solution stirred at room temperature/4 h, until no more precipitate is formed. A 1:1 mixture of hexane/$Et_2O$ is added to complete precipitation. The orange-colored precipitate is filtered off and extracted with $CH_2Cl_2$. The $CH_2Cl_2$ extracts are nearly completely evaporated and then treated with hexane/$Et_2O$ to precipitate the pure salt 7b (1.71 g, 88%; Scheme 6).

The salt 7b (4.72 g, 6.48 mmol) and cinnamaldehyde (8.6 g, 65 mmol) are stirred under an atmosphere of Ar at room temperature/3 d in the 1:1 two-phase system $CH_2Cl_2$/2N aq.NaOH (600 ml). The originally developed deep-red color changes to orange within 3 d. The basic phase is extracted with $CH_2Cl_2$ and the extracts washed with water and dried ($Na_2SO_4$). The residue of the dried extracts is chromatographed on silica gel (hexane/$Et_2O$ 9:1) to yield the crystalline (1'E,3'E)-isomer 8b which is re-crystallized from hexane/$Et_2O$ 1:1 (1.5 g, 50%); m.p. 159.4–161.4°). From the mother liquor crystallizes, after a longer period at 4° C., a small amount of the (1'Z,3'E)-isomer cis-8b (0.13 g, 4%); m.p. 112.9–113.7°).

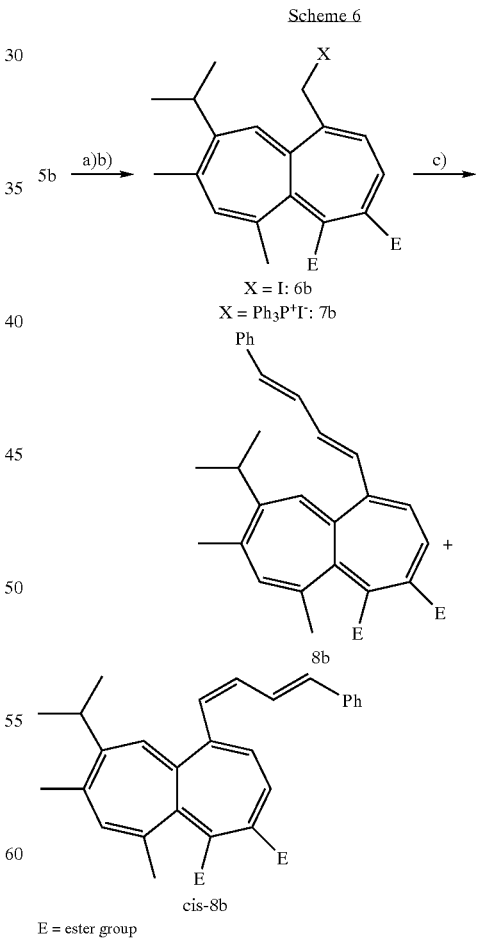

Scheme 6

X = I: 6b
X = $Ph_3P^+I^-$: 7b

E = ester group

The $^1$H-NMR spectrum ($CDCl_3$) of the (1'E,3'E)-isomer 8b resemble very much that of the corresponding 1-[(E)- styryl] analogue with the exception of the olefinic region which show two additional coupled H-atoms with H—C(1') at 6.54 (d, J$_{vic}$=15.0 Hz), H—C(2') at 6.39 (dd, J$_{vic}$=15.0 and 10.5 Hz), H—C(3') at 6.B3 (dd, J$_{vic}$=15.5 and 10.5 Hz), and H—C(4') at 6.57 ppm (d, J$_{vic}$=15.5 Hz). The (1'Z,3'Z)-isomer cis-8b exhibited the signals of the butadienyl-side chain at 6.97 (CDCl$_3$; dd, J$_{vic}$=15.3 and 11.3 Hz; H—C(3')), 6.52 (d, J$_{vic}$=15.3 Hz; H—C(4')), 6.17 (t-like, Å J$_{vic}$=23.3 Hz; H—C(2')), and 6.08 ppm (d, J$_{vic}$=12.0 Hz; H—C(1')).

Irradiation of 8b with light of 1=(439±10) nm (interference filter; Schott Schleiffer AG) at 10° in hexane solution do not lead to the formation of the DBS isomer 8a in detectable amounts (HPLC).

EXAMPLE 4

Double-bond shift of dimethyl 6,8,10-trimethyl-5-[(E)-2-phenylethenyl]-heptalene-1,2- and dimethyl 6,8,10-Trimethyl-1-[(E)-2-phenylethenyl]-heptalene-4,5-dicarboxylate (11a' and 11b', respectively)

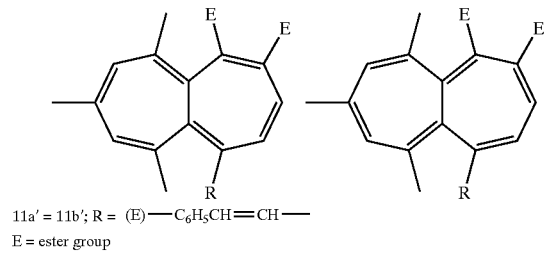

11a' = 11b'; R = (E)—C$_6$H$_5$CH═CH—
E = ester group

Heating of 11b' at 60–80° do not lead to the formation of its DBS isomer 11a' (HPLC and $^1$H-NMR prove; limit of detection of 11a'≧0.5%). However, irradiation of 11b' in hexane with light of a 366-nm-fluorescence tube establishes a photostationary state consisting of 68% of 11b' and 32% of 11a'. The photostationary state could be shifted to 20% of 11b' and 80% of 11a' when the irradiation is performed through a cut-off filter of an aqueous 1 N NaNO$_2$ solution (λ>400 nm; with a high-pressure mercury lamp). Heating of this solution at 60° transformes 11a' quantitatively again into 11b'.

$^1$H-NMR (300 MHz, CDCl$_3$) of 11a': 7.46–7.22 (m, 5 arom. H; 6.95 (d, J(3,4)=12.0, H—C(4)); 6.82 (d, J=16.3, PhCH═CH); 6.80 (d, J(4,3)=12.0, H—C(3)); 6.58 (d, J=16.3, PhCH═CH); 6.17 (s, H—C(9)); 6.13 (s, H—C(7)); 3.85, 3.78 (2s, 2 MeOCO); 2.23 (s, Me-C(6)); 2.05 (s, Me-C(8)); 1.75 (s, Me-C(10)). $^1$H-NOE (400 MHz, CDCl$_3$): 2.13 (Me-C(6))→6.82 (s; d, J=16.3, H—C(1')), 6.14 (s, H—C(7)); 6.58 (H—C(2'))→7.41 (m, 2 H$_O$ of Ph), 6.95 (s, H—C(4)); 6.95 (H—C(4))→6.80 (s, H—C(3)), 6.58 (s, H—C(2')). These results demonstrate that 11a' exists in solution almost exclusively in the s-trans-conformation with respect to its structural segment C(2')═C(1')-C(5)═C(5a).

EXAMPLE 5 dimethyl (−)-(P)- and (+)-(M)-6,8,10-trimethyl-5-[(E)-2-phenylethenyl)-heptalene-1,2-dicarboxylate ((−)-(P)-11a' and (+)-(M)-11a'

Irradiation of 11b' in hexane in the described manner leads to a photostationary state with 20% of 11b' and 80% of 11a'. Chromatography on the Chiralcel OD column with hexane/7% 2-PrOH (flow rate 0.5 ml/min) results in a partial separation of (−)-(P)- and (+)-(M)-11a' (separation factor 50%; t$_R$ ((M)/(P))=1.03) and no separation of (−)-(P) and (+)-(M)-11b' (t$_R$ (MP)-11b'/(P)-11a')=1.27). Two consecutive separations of the "photo"-mixture (1.8 mg leads to pure (−)-(P)- and (+)-(M)-11a'.

CD-spectrum (circular dichroism) of (−)-(P)-11a' (hexane; extrema in mdeg): 500 (0), 400sh (−10.1), 350 (−17.1), 320 (0), 285 (100.3), 254 (0), 249 (−6.1), 244 (0), 237sh (10.7), 233.5 (12.7), 226 (0), 213 (−31.5), 208 (0).

CD-spectrum (circular dichroism) of (+)-(M)-11a' (hexane; extrema in mdeg): 500 (2.8), 400sh (12.4), 350 (19.1), 319 (0), 285 (−102.6), 255 (0), 249 (6.9), 245 (0), 238sh (−9.8), 234 (−11.9), 227 (0), 213 (36.0), 208 (0).

EXAMPLE 6 dimethyl (−)-(P)- and (+)-(M)-6,8,10-Trimethyl-1-[(E)-2-phenylethenyl]-heptalene-4,5-dicarboxylate ((−)-(P)-11b' and (+)-(M)-11b')

The probes of (−)-(P)-11a' and (+)-(M)-11a' (see preceeding example) are dissolved in toluene (0.5 ml) and heated at 80°. Following the thermal isomerization with HPLC indicated that (−)-(P)-11a' and (+)-(M)-11a' gave within 1.75 h quantitatively (−)-(P)-11b' and (+)-(M)-11b', respectively.

CD-spectrum (circular dichroism) of (−)-(P)-11b' (hexane; extrema in Δε with respect to ε=2.6915·10$^4$ lmol$^-$$_1$cm$^{-1}$ of pure (MP)-11b' in hexane): 550 (0), 402.6 (−42.70), 348.6 (0), 306.4 (50.60), 263.8 (Min, 8.1), 251.6 (24.66), 237.0 (Min, 2.4), 222.2 (22.50), 210.6 (0);

CD-spectrum (circular dichroism) of (+)-(M)-11b' (hexane; extrema in Δε): 550 (0), 401.6 (44.90), 348.4 (0), 306.4 (−52.81), 263.6 (Max, −8.6), 251.4 (−25.70), 237.0 (Max, −2.5), 221.2 (−23.37), 210.4 (0);

EXAMPLE 7

Preparation of methyl 1,6-dimethyl-9-i-propyl-[(E)-4-phenyl-butandienyl]heptalene-5-carboxylate and methyl 1,6-dimethyl-9-i-propyl-((Z)-4-phenyl-butandienyl]heptalene-5-carboxylate Preparation of carbaldehyde 11b: Pseudo-ester 10b (0.100 g, 0.29 mmol) is dissolved in THF (5 ml) and cooled to −78° C. Under stirring and N$_2$ a 1M solution of DIBAH in hexane (0.9 ml, 0.87 mmol) is added dropwise. After additional stirring for 30 min at −78° C., a solution of (COOH)$_2$.H$_2$O in Et$_2$O is added slowly. After warming to 20° C., water is added to the reaction mixture and the organic material taken up in Et$_2$O. The Et$_2$O extracts are washed with water and dried (Na$_2$SO$_4$). Chromatography on silica gel (hexane/Et$_2$O 4:1) affords a pure 3:1 mixture (0.073 g, 80%) of 11b and 12b. Carbaldehyde 11b is characterized by its $^1$H-NMR spectrum (CDCl$_3$), showing the signal for the H-atom of the carbaldehyde group at 9.37 ppm and the signal for the H-atoms of MeOCO—C(5) at 3.71 ppm. The known lactone 12b is also characterized by its reported $^1$H-NMR spectrum.

Preparation of the heptalenes 13a and 13b: The aforementioned 3:1 mixture of 11b and 12b (0.5 g, 1.61 mmol) and cinnamyl-triphenyl-phosphonium bromide (1.11 g, 2.43 mmol) are reacted in the two-phase system CH$_2$Cl$_2$/2N NaOH (200 ml) as described in example 3. Two subsequent chromatographies (the first one to remove Ph$_3$PO) on silica gel (hexane/Et$_2$O 7:1) give a 3:7 mixture (0.204 g, 31%) of 13a and cis-13a with the corresponding DBS isomers 13b and cis-13b in thermal equilibrium (see Scheme 8). The mixture is dissolved in hexane/Et$_2$O 1:1 (10 ml) and stirred with a catalytic amount of I$_2$ at room temperature/6 h, whereby the cis-isomers are isomerized quantitatively into the thermal equilibrium mixture consisting of 70% 13a and 30% of 13b.

Structure assignments: The described isomerizations can easily be followed by $^1$H-NMR spectroscopy since all four isomers show inter alia different chemical shifts (CDCl$_3$) for their methoxycarbonyl groups; 3.69 (13b), 3.63 (13a), 3.60 (cis-13a), and 3.54 ppm (cis-13b). The (1'E,3'E)-configuration of the 4-phenylbutadienyl-side chain of 13a is indicated by the corresponding vicinal coupling constants in the $^1$H-NMR spectrum (CDCl$_3$): 7.64 (d, J$_{vic}$=15.4 Hz; H—C(4')), 6.98 (dd, J$_{vic}$=15.5 and 10.5 Hz; H—C(2')), 6.77 (dd, J$_{vic}$=15.5 and 10.7 Hz; H—C(3')), and 6.69 (d, J$_{vic}$=15.5 Hz; H—C(1')). The position of the C=C bonds at the heptalene perimeter is signified by the AB systems of H—C(3) and H—C(4) as well as of H—C(8) and H—C(9) with J$_{AB}$=12 Hz.

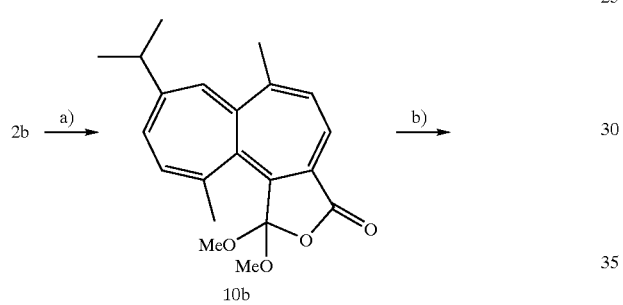

Scheme 7

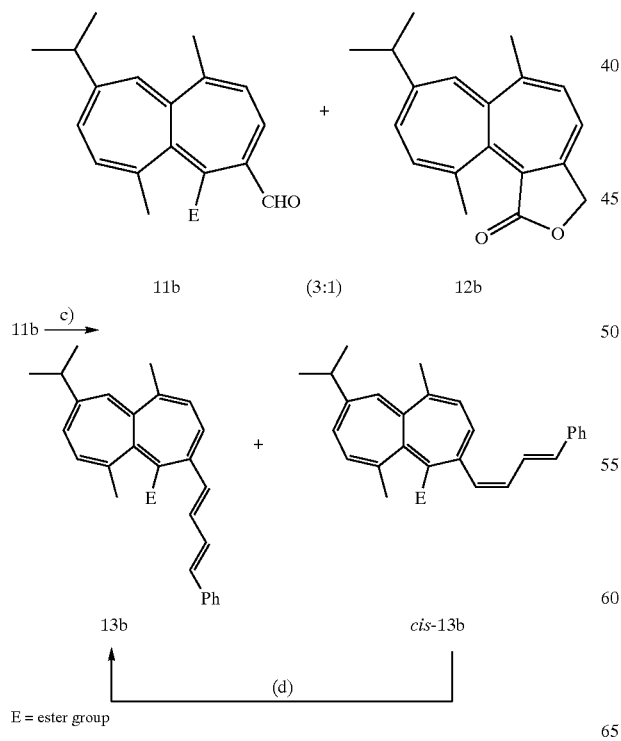

E = ester group

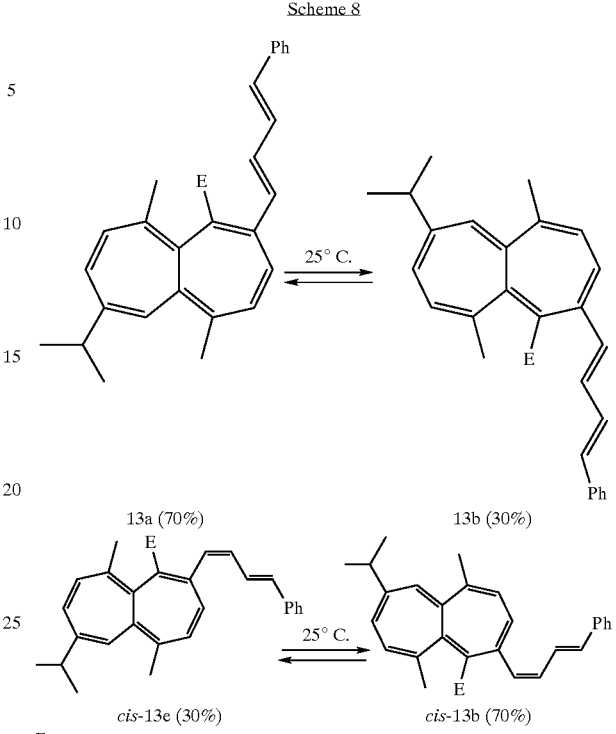

Scheme 8

13a (70%)   13b (30%)

cis-13e (30%)   cis-13b (70%)

E = ester group

EXAMPLE 8

Preparation of dimethyl 5-(4-Methoxyphenyl)-6,8,10-trimethylheptalene-1,2-dicarboxylate and dimethyl 1-(4-Methoxyphenyl)-6,8,10-trimethylheptalene-4,5-dicarboxylate (10a' and 10b', respectively)

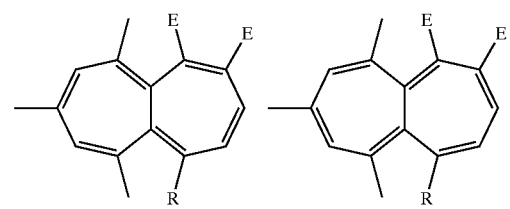

10a' = 10b'; R = 4-MeOC$_6$H$_4$
E = ester group 1-(4-Methoxyphenyl)-4,6,8-trimethylazulene (0.276 g; 1.00 mmol), dimethyl acetylenedicarboxylate (0.426 g; 3.00 mmol), and [RuH$_2$(PPh$_3$)$_4$] (0.058 g; 0.05 mmol) are dissolved in MeCN (5 ml) and heated in a closed Schlenk tube at 110° for 24 h. The workup and chromatography on silica gel (hexane/Et$_2$O 7:3) leads to 4 fractions containing dimethyl (E)-1-[3-(4-methoxyphenyl)-4,6,8-trimethylazulen-1-yl]ethene-1,2-dicarboxylate ((E)-21'; 0.0084 g, 2%), dimethyl 1-(4-methoxyphenyl)-5,6,8-trimethylacenaphthylene- 3,4-dicarboxylate (22'; 0.0083 g, 2%), 10b' (0.0125 g, 3%), and dimethyl 4,6,8-trimethylazulene-1,2-dicarboxylate (0.152 g, 53%).

Data of (E)-21': Brown crystals, m.p. 122'.9–123.8° (Et$_2$O/hexane). IR (KBr): 3020w, 2980w, 2940w, 2820w, 1720s, 1710s, 1610s, 1570m, 1550w, 1525w, 1500s, 1430s, 1370w, 1315m, 1280s, 1240s, 1180s, 1170s, 1150s, 1110m, 1100w, 1060w, 1020s, 990w, 940w, 890w, 870w, 840w, 830m, 800w. $^1$H-NMR (300 MHz, CDCl$_3$): 7.30 (d, J=8.9, 2 arom. H); 7.06 (s, MeOCOCH=), 6.96 (s, H—C(7)); 6.93 (d, J=8.9, 2 arom. H); 6.92 (s, H—C(5)); 6.90 (s, H—C(2)); 3.87 (s, MeO); 3.78, 3.51 (2s, 2 MeOCO); 2.75 (s, Me-C(8)); 2.55 (s, Me-C(6)); 2.42 (s, Me-C(4)). EI-MS: 419 (28), 418 (100, M$^+$), 404 (11), 403 (40), 359 (60, [M–COOMe]$^+$).

Data of 22': Yellow crystals, m.p. 190.6–191.0 (Et$_2$O/hexane). IR (KBr): 2980w, 2940w, 2840w, 1740s, 1720s, 1610m, 1570w, 1540w, 1490m, 1450m, 1440m, 1430m, 1400m, 1370m, 1330w, 1280m, 1270s, 1240s, 1200s, 1180s, 1150m, 1110w, 1070w, 1050m, 1040m, 1030m, 990w, 970w, 900w, 870w, 840m, 820w, 800w. $^1$H-NMR (300 MHz, CDCl$_3$): 7.46 (d, J=8.7, 2 arom. H); 7.13 (s, H—C(7) or H—C(2)); 7.11 (s, H—C(2) or H—C(7)); 6.99 (d, J=8.7, 2 arom. H); 3.99, 3.97 (2s, 2 MeOCO); 3.89 (s, MeO); 2.83 (s, Me-C(5)); 2.80 (s, Me-C(6)); 2.31 (s, Me-C(8)) CI-MS (NH$_3$): 436 (7), 434 (7, [M+NH$_4$]$^+$), 419 (10), 418 (46), 417 (100, [M+1]$^+$), 416 (21'), 389 (7), 388 (23), 387 (86), 389 (28), 385 (93). Anal. calc. for C$_{26}$H$_{24}$O$_5$ (416.48): C 74.98, H 5.81; found: C 74.71, H 5.96.

Data of 10b': Orange crystals, m.p. 169.5–170.00 (Et$_2$O/hexane). IR (KBr): 1720s, 1640w, 1600w, 1550w, 1500s, 1440m, 1380w, 1370w, 1300m, 1280s, 1250s, 1200w, 1180s, 1160w, 1110w, 1040m, 1030w, 820w, 780w. $^1$H-NMR (300 MHz, CDCl$_3$): 7.73 (d, J(2,3)=6.3, H—C(3)); 7.37 (d, J=6.9, 2 arom. H); 6.88 (d, J(3,2)=6.3, H—C(2)); 6.82 (d, J=6.9, 2 arom. H); 6.20 (s, H—C(9)); 6.14 (s, H—C(7)), 3.80 (s, MeO); 3.75, 3.71 (2s, 2 MeOCO); 2,10 (d, J(7, Me-C(6))=1.1, Me-C(6)); 1.93 (d, J(9, Me-C(8))= 1.1, Me-C(8) ); 1.46 (s, Me-C(10)). EI-MS: 419 (31), 418 (100, M$^+$), 403 (10), 387 (10), 371 (13), 359 (14, [M–COOMe]$^+$), 327 (11, [M–COOMe–MeOH]$^+$), 300 (6), 286 (9, [M–p-MeOC$_6$H$_4$C≡CH]$^+$), 285 (6), 277 (9), 276 (37, [M–E–C≡C–E]$^+$).

Heptalene 10b' in hexane does not give its DBS isomer 10a' on heating. However, on irradiation with 366-nm-light of a fluorescence tube, it easily rearranges to 10a' and forms a photostationary state which consists in 62% of 10b' and 38% of 10a'. $^1$H-NMR (300 MHz, CDCl$_3$) of 10a' (in the presence of 62% of 10b'): 7.07 (d, J=8.8, 2 arom. H); 6.83 (m, 2 arom. H and H—C(4)); 6.64 (d, J(4,3)=11.9, H—C(3)); 6.24 (s, H—C(9)); 5.99 (s, H—C(7)); 3.87, 3.73 (2s, 2 MeOCO); 3.82 (s, MeO); 2.10 (s, Me-C(8)); 1.75 (s, Me-C (10)); 1.64 (s, Me-C(6)).

EXAMPLE 9

Preparation of methyl 6-methyl-9-i-propyl-[1,4-bis (E)-4-phenyl-butandienyl]heptalene-5-carboxylate (16a/16b) and its DBS-isomer The procedures so far described can also be applied for the synthesis of more extended, switchable π-systems as represented by the heptalenes 16a and 16b. The synthetic procedures are summarized in Scheme 9.

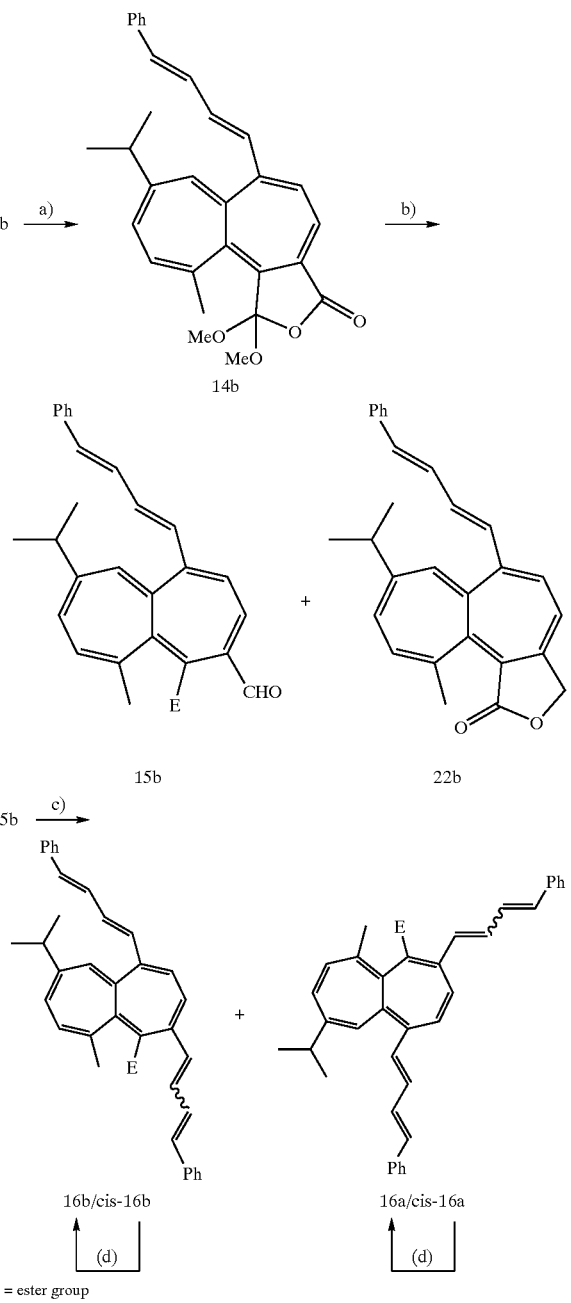

Scheme 9

Preparation of the pseudo-ester 14b: To a solution of LiOH.H$_2$O (5.0 g, 0.12 mol) in a mixture of MeOH (200 ml) and H$_2$O (30 ml) is added the heptalenediester 8b (2.50 g, 55 mmol) from example 3 and heated for 1.5 h under reflux. Water (50 ml) and 2N HCl is added until all Li salts are neutralized and the 4-carboxylic acid is preci-pitated. The acid is filtered off, washed with water and dried in vacuo (2.20 g, 88%); m.p.>150° C., decomp. into the corresponding cyclic anhydride. $^1$H-NMR (CDCl$_3$): 3.71 (s, MeOCO—C(5)).

The 4-carboxylic acid (0.13 g, 0.30 mmol) is dissolved in MeCN (0.8 ml) and added at 0° C. to the iminium salt formed in MeCN (1.7 ml) from DMF (0.072 g, 0.56 mmol) and oxalyl chloride (0.143 g, 1.95 mmol) at 0° C. After 5 min at 0° C., MeOH (5 ml) is added and then water (5 ml). The organic material is extracted with Et₂O and the extracts washed with water and dried (Na₂SO₄). The solid residue of the dried Et₂O extracts is recrystallized from Et₂O/hexane to give the pure pseudo-ester 14b (0.110 g, 81%); m.p. 180.2–180.7° C. ¹H-NMR (CDCl₃): 3.46 and 3.16 (2 s, 2 MeO). The DBS isomer 14a, which is present to an extent of ca. 1%, shows the signals of its MeO groups at 3.60 and 3.30 ppm.

Carbaldehyde 15b: The reduction of the pseudo-ester 14b (1.50 g, 3.30 mmol) with 1M DIBAH in hexane (9.9 ml, 9.9 mmol) is performed as described in example 7. Chromatography of the crude product mixture on silica gel (hexane/Et₂O 7:1) leads, after recrystallization from Et₂O/hexane, to pure carbaldehyde 15b (0.45 g, 30%) and lactone 22b (0.90 g, 64%). Carbaldehyde 15b: m.p. 138.4–140.0° C. ¹H-NMR (CDCl₃): 9.42 (s, OHC—C(4)); 3.73 (s, MeOCO—C(5)). Lactone 22b: m.p. 182.1–183.2° C. ¹H-NMR (CDCl₃): A thermal eqilibrium mixture of ca. 75% of 22a and ca. 25% of 22b is formed.

Heptalene 16a and 16b: Carbaldehyde 15b (0.25 g, 0.55 mmol) and cinnamyl-triphenylphosphonium bromide (1.50 g, 3.30 mmol) are reacted in the two-phase system CH₂Cl₂/2N NaOH (30 ml/30 ml) as described in example 3. Chromatography on silica gel (hexane/Et₂O 9:1) leads to a 1:0.37:0.07:0.07 mixture of cis-16b:16b:16a:cis-16a (0.14 g, 50%). The four isomers are characterized by the ¹H-NMR signals (CDCl₃) of their MeOCO group: 3.71 (s, 16b), 3.64 (s, 16a), 3.61 (s, cis-16a), 3.56 (s, cis-16b).

When a solution of the discussed mixture in hexane/Et₂O 1:1 (10 ml) is stirred in the presence of a catalytic amount of I₂ at room temperature/6 h, both cis-isomers are completely isomerized into the thermal equilibrium mixture of ca. 78% of 16b and ca. 22% of 16a.

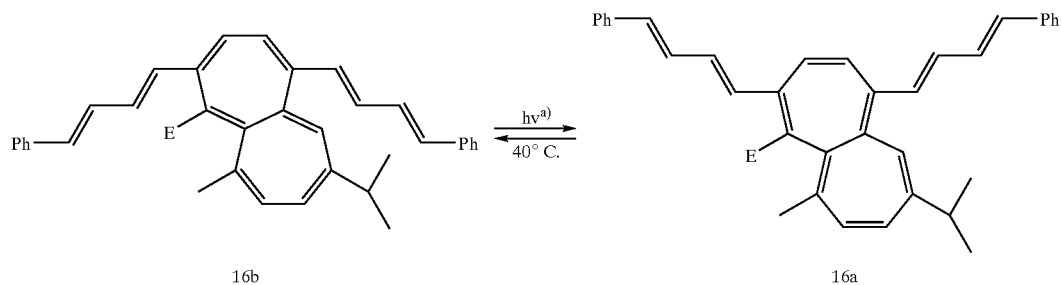

The UV/VIS spectra of 16a, respresenting the off-state of this 1,4-CS system and 16b, equivalent with the on-state, have already been discussed in connection with figure 1A and 1B.

EXAMPLE 10

Preparation of methyl 6-methyl-9-iso-propyl-[1-(E)-(2-(p-methoxy)phenylethenyl)-4-(E)-4-(p-nitro)-phenyl-butandienyl]heptalene-5-carboxylate (21a/21b) and its DBS-isomer An even more delocalized system containing donot-acceptor perimeter substituents in 1,4-relation, the heptalenecarboxylate 21b carrying an [(E)-4-methoxy-styryl] group at C(1) and an [(E)-4-nitrostyryl] moiety at C(4) shall be described herein. The procedure for the synthesis of 21a/21b is shown in scheme 11.

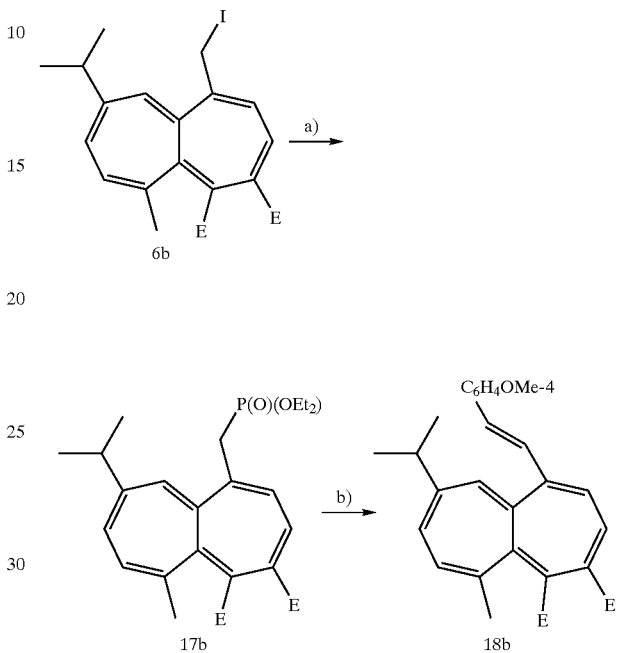

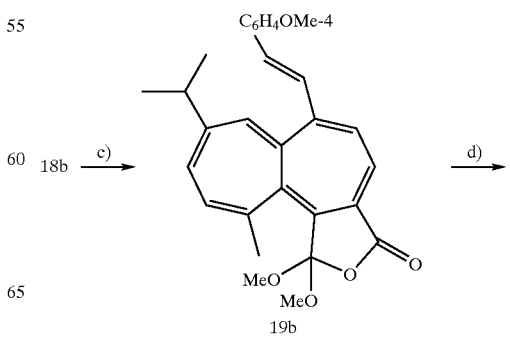

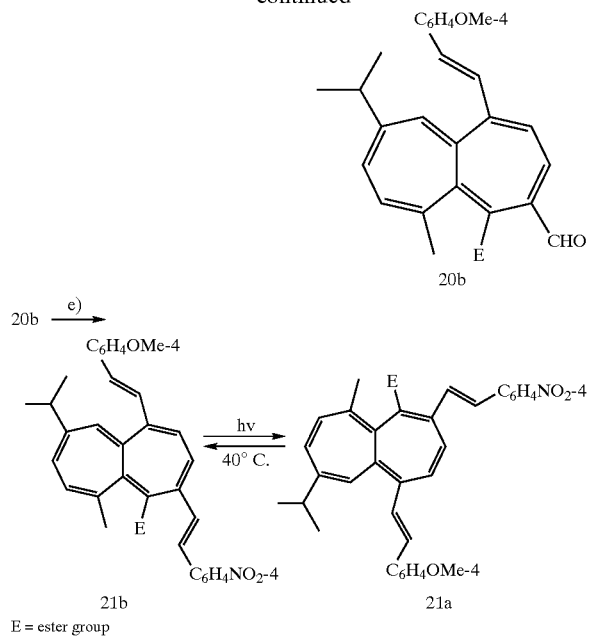

Dimethyl 9-isopropyl-1-[(E)-2-(4-methoxyphenyl)ethenyl]-6-methylheptalene-4,5-dicarboxylate (18b): Iodide (1.30 g, 2.80 mmol), which is obtained when the phosphonium salt formation of 7b according to example 3 (Scheme 6) is performed in two steps, is dissolved in $CH_2Cl_2$ (20 ml) and added dropwise to triethyl phosphite (5 ml) heated at 90° C./600 mbar. $CH_2Cl_2$ and the formed EtI are distilled off under these conditions. The reaction mixture is heated at 90° C./400 mbar for additional 40 min. Then, at 90° C./30 mbar, the excess triethyl phosphite is distilled off. The formed heptalene phosphonate 17b is used without further purification in the next step (Horner-Wadsworth-Emmons reaction).

Phosphonate 17 b is dissolved in THF (20 ml) and cooled to −78° C. To this solution sodium bis(trimethylsilyl) amide (0.60 g, 3.3 mmol) in THF (10 ml) is added. After 1 h stirring at −78° C., 4-methoxybenzaldehyde (2.3 ml, 16.8 mmol) is added and the temperature raised to −18° C. At this temperature stirring is continued for 20 h. The reaction mixture is neutralized with 2N HCl and extracted with $Et_2O$. The $Et_2O$ extracts are washed with water and dried ($Na_2SO_3$). The residue (0.90 g, 70%) of the dried $Et_2O$ extracts is recrystallized from $Et_2O$/hexane 2:1 to yield pure 18b (0.60 g, 47%); m.p. 160.9–162.2° C. The spectral data of 18b have already been reported (H.-J. Hansen, Helv. Chim. Acta 1994, 77, 1940).

Pseudo-ester 19b: Diester 18b (0.95 g, 2.07 mmol) is saponified with $LiOH.H_2O$ (1.90 g, 45 mmol) in MeOH (76 ml) and $H_2O$ (10 ml) as described in example 9. The 4-carboxylic acid of 18b is obtained in 72% yield.

This acid (0.45 g, 1.01 mmol) is reacted with the iminium salt formed from DMF and oxalyl chloride as described in example 6. The described work-up gives the pure pseudo-ester 19b (0.40 g, 80%) after chromatography; m.p. 150.2–151.0° C. $^1$H-NMR ($CDCl_3$): 3.82 (s, MeO—Ar), 3.46 and 3.16 (2 s, MeO of pseudo-ester).

Carbaldehyde 20b: Pseudo-ester 19b (2.00 g, 4.40 mmol) is dissolved in toluene (150 ml) and cooled to −78° C. At this temperature, a 2M DIBAH solution in hexane (2.2 ml, 4.40 mmol) is added dropwise under stirring. After additional stirring for 15 min, the reaction mixture is added to precooled MeOH (50 ml) and then warmed up to room temperature. A small amount of $H_2O$ (13.2 mmol) is added and the precipitated Al salts are filtered off and washed with $Et_2O$. The filtrate is dried ($Na_2SO_4$) and evaporated. The solid residue is recrystallized from hexane/$Et_2O$ 1:1 to give the pure carbaldehyde 20b (in total 1.51 g, 80%); m.p. 172.9–174.9°. $^1$H-NMR ($CDCl_3$): 9.43 (s, OHC—C(4)), 3.82 (s, MeO—Ar), 3.73 (s, MeOCO—C(5)).

Heptalene 21a and 21b: Carbaldehyde 20b (0.150 g, 0.35 mmol) and p-Nitrobenzyl-triphenylphosphonium bromide (1.6 g, 3.5 mmol) are reacted in the two-phase system $CH_2Cl_2$/2N NaOH (15 ml/15 ml) as described in example 3. Chromatography on silica gel (hexane/$Et_2O$ 4:1) gives in a first fraction the thermal equilibrium mixture of 14% of 21a and of 86% of 21b (5 mg, 2.6%). $^1$H-NMR ($CDCl_3$): 3.82 (s, MeO—Ar of 21a), 3.81 (s, MeO—Ar of 21b), 3.69 (s, MeOCO—C(1) of 21a), 3.67 (s, MeOCO—C(5) of 21b).

Figure 2A:
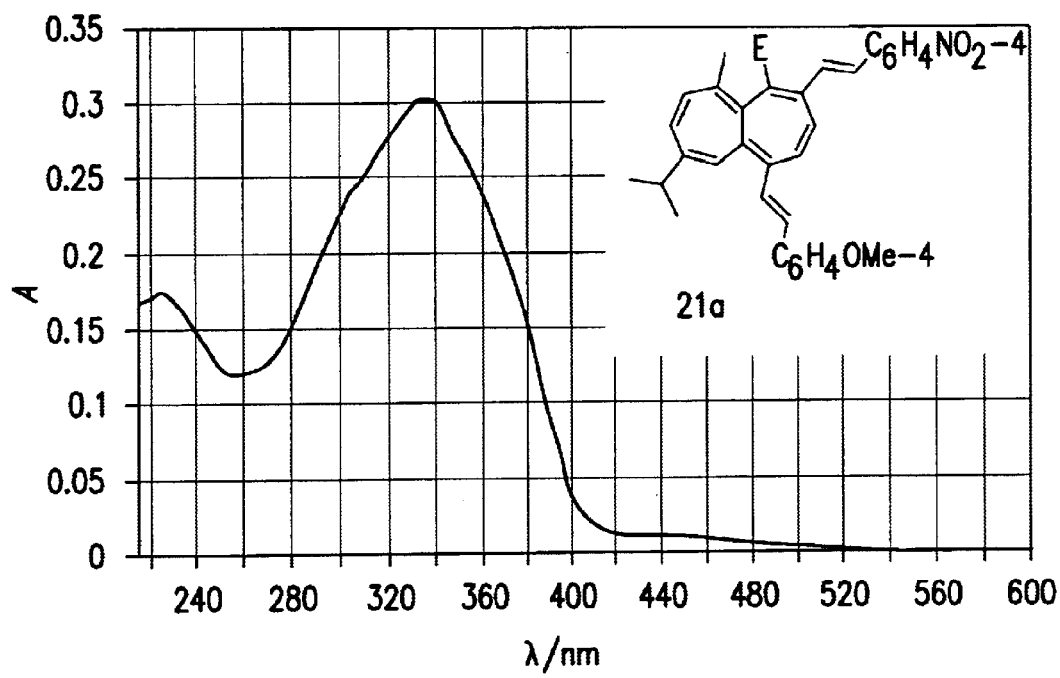
Figure 2B:
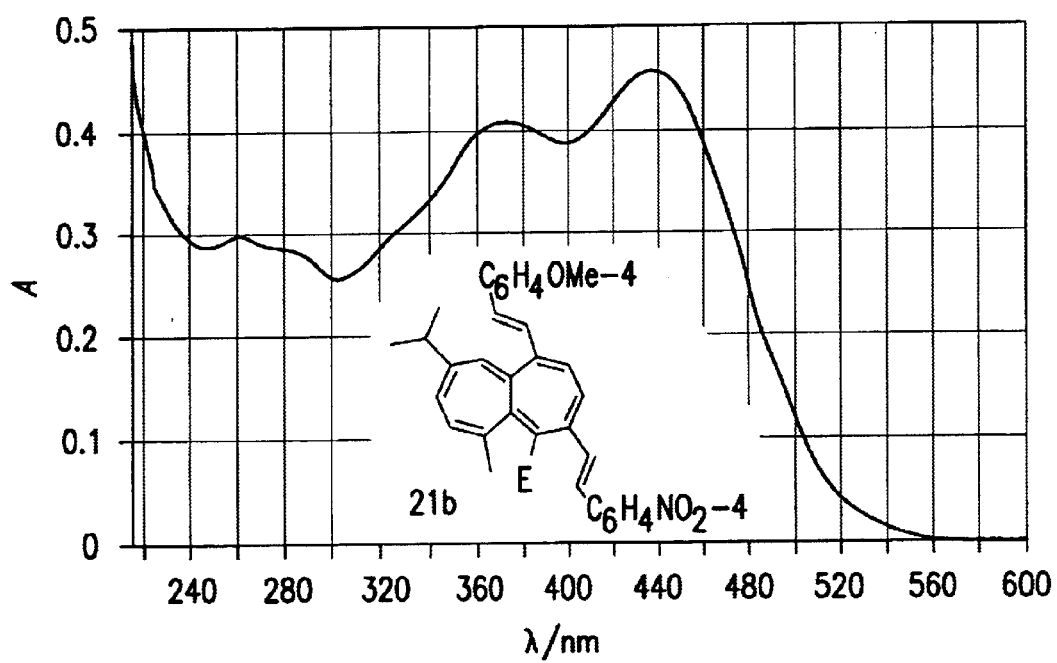

The UV/VIS spectra of 21a and 21b are shown in figures 2A and 2B. The habitus of the spectrum of 21a resembles very much that of 16a. However, the main absorption band of 21a at 340 nm is appreciably broader than that of 16a at 345 nm. This is chiefly due to the fact that the heptalene band II of 21a is much more intense than in 16a. Also the heptalene band I of 21a at ca. 440 nm seems to be more intense than in 16a. Moreover, an additional absorption band is recognizable in 21a sitting as a shoulder on the low-wavelength flank of the heptalene band III. A comparable band in 16a at 280 nm is much less intense. The switch of the p-bonds in 21a induces again a tremendous change in the UV/VIS spectrum of the new heptalene 21b. The most intense band appears now at 445 nm. It must have its origin in the heptalene band I and, possibly, II (vide supra). The strong absorption at 375 nm (360 nm for 16b) can be assigned to the heptalene band III, followed by a shoulder at the low-wavelength flank at ca. 330 nm which may correlate with the shoulder at ca. 300 nm of 21a.

In conclusion, the absorption difference of both 1,4-CS systems, i.e., 16a⇌16b and 21a⇌21b, for their longest-wavelength bands at 440 and 445 nm, respectively, is with 0.03:1 approximately the same. These pronounced absorption differences are already readily noticeable in diluted solutions with the bare eye.

EXAMPLE 11

Method to Prepare a Rewritable Compact Disk Comprising Compounds 16a/16b as Material for Data Storing A polycarbonate disk having a diameter of 5.25 inch and a thickness of 2 mm is coated with a 0.25 μm solid layer of 16a/16b by evaporating a mixture of 16a/16b in a high vacuum chamber onto its surface, thus affording an absorbence A at approximately 1 at 440 nm, as referred to 100% conjugative on-state. A second disk is coated by standard procedures with an $Al_2O_3$ protected reflective aluminum layer. The two disks are bonded together with the heptalene and aluminum layers at the inside of the sandwich structure. Writing (bleaching) of the disk is performed by focusing a modulated IR-laser onto the heptalene layer while simultaneously irradiating the heated spot by light in the 430 to 550 nm range. The intensity of the IR-laser is adjusted so as to impart sufficient conformational mobility to the heptalene system 16a/16b for the photochemically induced DBS process to occur. Erasing (coloring) is achieved by irradiating a spot, which is heated as described above for increasing the mobility of the heptalene molecules being at the conjugation off-state by light having a wavelength of 350 nm or by simply recreating the 16a/16b by spotwise heating with a modulated IR-laser.

The process is perfectly analogous for writing/erasing procedures of the traditional and well-known magneto-optical disks and similar considerations for spot size, spinning speed, guiding the write/read head, and data transfer rates apply.

Reading of the data is achieved by focusing the light of a read laser with light in the 430 to 550 nm range of the spinning disk and registering the intensity modulation of the light reflected from the aluminum layer.

A doubling of the data density on the disk can be achieved by using two orthogonal directions of linear polarized writing light and separately detecting the reflected intensity of two orthogonal polarizations of the reading light.

EXAMPLE 12

Method to Prepare a Rewritable Compact Disk Comprising Compounds 21a/21b as Material for Data Storing A glass disk having a diameter of 3.33 cm (5.25 inch) and a thickness of 2 mm is coated with a 0.5 mm solid layer of a $10^{-3}$ molar solution of 21a/21b in methylene chloride, thus affording a solid layer of heptalene is molecules with an absorbence A of approximately 1 at 440 nm, as referred to 100% conjugative on-state. A second disk is coated by standard procedures with an $Al_2O_3$ protected reflective aluminum layer. The two disks are bonded together with the heptalene and aluminum layers at the inside of the sandwich structure. Writing, erasing and reading is accomplished as in example 11.

EXAMPLE 13

Method to Prepare a Rewritable Compact Disk Comprising Compounds 21a/21b, Embedded in a Methylacrylate Matrix, as Material for Data Storage A $10^{-3}$ molar solution of 21a/21b in methylene chloride is prepared in a degassed two-component or light curable methylmethacrylate embedding mass. The mass is sandwiched as a 2 $\mu$m thick layer between two 3.33 cm (5.25 inch), 2 mm thick glass disk, with one of the disks coated with an $Al_2O_3$ protected reflective aluminum layer turned to the inside of the sandwich structure. After the curing, writing, erasing and reading are performed as described in example 11.

EXAMPLE 14

Method to Prepare a Holographic Rewritable Memory Comprising Compounds 21a/21b, as Material for Data Storage A $5\times10^{-3}$ molar concentration of 21a/21b is prepared in a degassed two-component or light-curable methylmethacrylate embedding mass. A volume holographic disk is prepared by coating a 8.83 cm (3.5 inch) glass disk with a 100 $\mu$m thick layer of the embedding mass containing the heptalene molecules. A spatially modulated object beam with a wavelength being at 450 nm is created in the usual manner by passing it through a liquid crystal spatial light modulator of 640×480 pixels, thus carrying about 307,200 bits of information. Said object beam is brought to interference with a reference beam of identical wavelength of approximately 1.5 mm$^2$ on the 10 $\mu$m layer containing the heptalene molecules. The spot is temporarily heated by an IR-laser to a temperature where photochemical interconversion of the conjugation on-state and off-state actually occurs, but not sizable thermal equilibration of the photochemically created conjugation on-state/off-state distribution. After switching off the object, reference and IR-laser beams, a holographic interference pattern is present in the form of more off-state heptalene molecules being present in zones where additives interference of the recording beams occurred than in zones where subtractive interference occurred, i.e. bleaching for light of wavelengths between $\lambda$=400 nm and $\lambda$=550 nm has taken place in additive zones. The hologram can be read out in the usual manner, by generating an object beam through irradiation of the hologram with a reference beam and recording the object beam pattern with a 640×480 pixel containing charge coupled device.

Several holograms are superimposed on the same location by the well-demonstrated angular multiplexing technique. After exhausting the recording potential of a given spot, the disk is turned to a new spot and the same procedure is repeated. The information is erased from the disk 1.5 mm$^2$ spot by 1.5 mm$^2$ spotwise by heating each spot with an IR-laser to a temperature where thermal equilibration of the heptalene on-state and off-state distribution in the embedding matrix occurs. Each erased spot is now ready for recording in the described manner.

EXAMPLE 15

Method to Prepare a Spatial Light Modulator Modulated by Light and Comprising Compounds 16a/16b, as Light Modulating Material A $4\times10^{-3}$ molar solution of the substituted heptalenes 16a/16b in diethyleneglycoldiethylether is placed in a 0.5 mm thick optical sample cell which provides a 1 square centimeter clear aperture and which is kept at an adjustable temperature. The temperature is adjusted just high enough, so that the transmission through the sample cell of a linearly polarized expanded probe beam with $\lambda$=450 nm is essentially blocked by being absorbed by the continuously (through thermal interconversion) regenerated on-state form of the heptalene molecules. A second signal light beam of the same or similar wave-length, linearly polarized perpendicularly to the probe beam, is combined with the latter by standard polarizing beam combining optics, so that it falls jointly with it on the entrance window of the sample cell. If the cell is made transparent—vide infra—the two superimposed beams pass jointly through the cell and are separated after the cell by standard polarizing beam splitting optics. The probe beam can thus be detected separately. Its spatial intensity distribution is analyzed by recording it with a standard light-sensitive charge-coupled (CCD) device having 640×480 pixels.

The signal beam, before being combined with the probe beam, passes through a liquid crystal spatial light modulator having 640×480 pixels. If all pixels are shut-off the CCD device will record essentially zero intensity in the probe beam. If individual pixels, or contiguous clusters of pixels are turned on, the light intensity of the signal beam combines with the light intensity of the probe beam at the corresponding areas of the heptalene containing sample cell, a higher proportion of the heptalene molecules is present in the off-state at these locations, more light of the probe beam passes through the cell and is detected by the CCD device.

Thus, the signal beam imprints its spatial intensity distribution on the probe beam. If the probe and the signal have their own spatial intensity distribution, the function performed by the cell corresponds to a logical "AND". Through an obvious optical modification, a self-switching of the probe beam is achieved, i.e. an optical flip-flop. The polarizing beam and splitting optics are replaced by non-polar optics and the signal beam at the entrance of the sample cell is generated by the portion split of the probe after it has left the sample cell.

What is claimed is:

1. Method for information storage and data processing comprising the step of thermo-inducing or photo-inducing double-bond shifts in substituted [4n]-annulenes which are substituted by at least one group comprising an extended conjugated π-electron system which is in conjugation with the π-electron system of the [4n]-annulene core, thus generating transitions between two different conjugation states with at least one substituent, resulting in different UV/VIS spectra of the double-bond shifted isomers of [4n]-annulene, which provides the possibility to use distinct conjugation states (conjugation on-state and conjugation off-state) for information storage and data processing, whereby a carrier system is present that allows the modulation of a multitude of the corresponding [4n]-annulene molecules for the permanent or erasable storage of their corresponding conjugative states.

2. Method according to claim 1, whereby the two different conjugation states are the conjugation on-state and conjugation off-state of the annulene core π-electrons relative to the substituent π-electrons.

3. Method according to claim 1, whereby said [4n]-annulenes are bicyclic [4n]-annulenes.

4. Method according to claim 3, whereby said bicyclic [4n]-annulenes are heptalenes.

5. Method according to claim 1, whereby the [4n]-annulenes are substituted in 1,2- or 1,4-position relative to each other by two groups having an extended and conjugated π-electron system.

6. Method according to claim 1, whereby a multitude of [4n]-annulene molecules are arranged in a 1-dimensional or in a 2-dimensional or in a 3-dimensional way and wherein said conjugation states are spacially non-uniformly modulated.

7. Method according to claim 6, whereby a holographic grating is generated by modulating said conjugation states.

8. Method according to claim 6, wherein the spacially non-uniformly modulated conjugation states are generated by a low-energy laser that provides for a local heating so bring the [4n]-annulenes into switching condition and whereby the laser light causes locally, if required, the switch from the conjugative on-state to the conjugative off-state.

9. Method according to claim 6, comprising further to said step of modulating a multitude of [4n]-annulene molecules in a 1-dimensional or 2-dimensional or 3-dimensional way and wherein said conjugation states are spacially non-uniformly modulated, a further step wherein at least one of the optical, electrical or magnetic properties being attributable to said switchable conjugation states is determined and processed.

10. Method according to claim 1, wherein the carrier comprises a low-melting glass or polycarbonates, polyacetates, methacrylates, styrenes and copolymers thereof, as well as copolymers with polymerisable [4n]-annulenes.

11. Method according to claim 1, wherein said conjugation states are determined by an optical read-out step.

12. Method according to claim 1, wherein the determination of the spacially non-uniformly modulated conjugation states is used for the optical reading of information.

13. Method according to claim 1, wherein the determination of the spacially non-uniformly modulated conjugation states is used for optical switching and computing.

14. Process of information storage and data processing by using substituted [4n]-annulenes which are substituted by at least one group comprising an extended conjugated π-electron system which is in conjugation with the π-electron system of the [4n]-annulene core undergoing thermally induced or photo-induced double-bond shifts thus generating or processing previously generated at least two different conjugation states with at least one substituent in selected regions of storage medium, whereby a carrier system is present that allows the modulation of a multitude of the corresponding [4n]-annulene molecules for the permanent or erasable storage of their corresponding conjugative state.

15. Substituted [4n]-heptalenes of the general formula (I) or (II) being optically and/or thermally switchable, based on thermal or photochemical double-bond shifts (DBS),

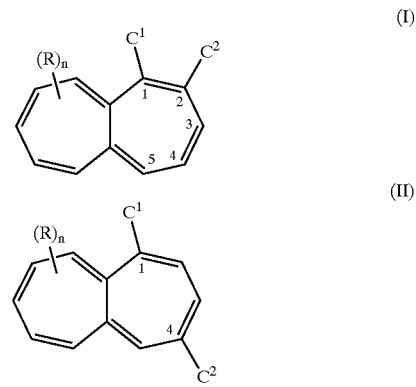

whereby $C^1$ and $C^2$ represent independently from each other a hydrogen atom, a substituted or unsubstituted $C_1$–$C_{12}$-alkyl group, a substituted or unsubstituted $C_1$–$C_{12}$-alkoxy group, a substituted or unsubstituted aryl-$C_1$–$C_{12}$-alkyl group, a substituted or unsubstituted $C_1$–$C_{12}$-alkenyl group, a substituted or unsubstituted $C_1$–$C_{12}$-conjugated alkenyl group, a substituted or unsubstituted $C_1$–$C_{12}$-alkinyl group, a substituted or an unsubstituted phenyl group, a substituted or an unsubstituted heterocyclic group, a cyano group, a nitro group, a thiocyanate group, a $C_1$–$C_{12}$-ester group being optionally polymerisable with copolymers, with the proviso that at least one of said substituents $C^1$ and $C^2$ contains an extended conjugated π-electron system which is in conjugation with the π-electron system of the heptalene core, and whereby said [4n]-heptalenes can comprise at least one further substituent R being selected from the above indicated groups with n being 0–8, provided that if one of the at least one further substituents R is an isopropyl group at the position 9 of the heptalene ring, the substituent at the position 6 must not be a methyl group, and with the proviso that heptalenes having the following substituents including their valence isomers are excluded:

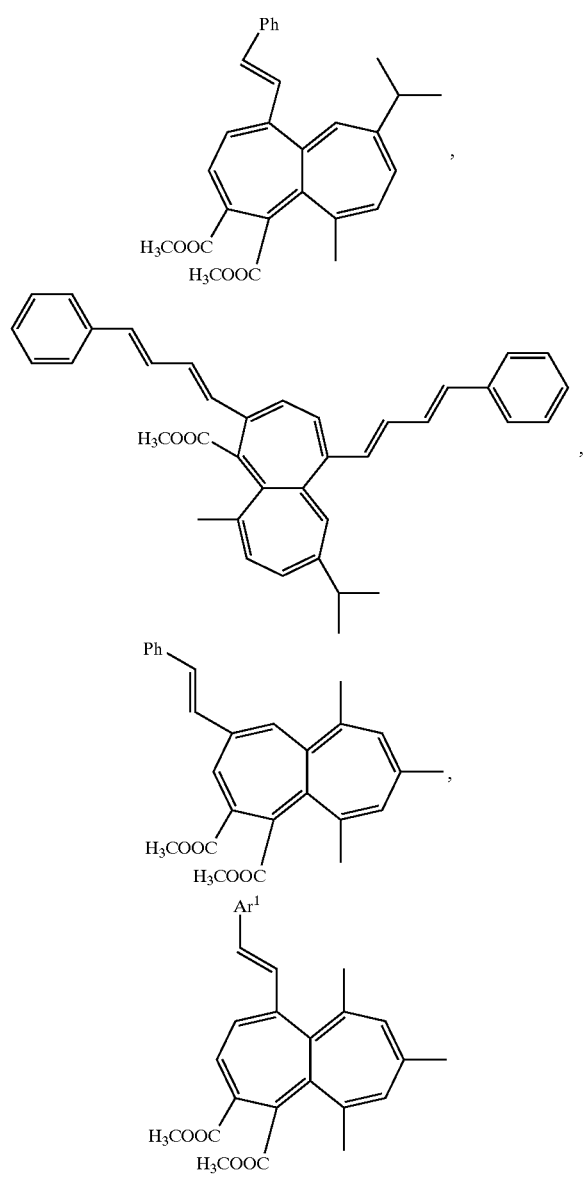

wherein Ar¹ is phenyl, 4-chloro phenyl or 4-methoxy phenyl, and

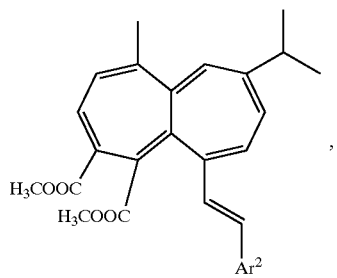

wherein Ar² is phenyl or 4-methoxy phenyl.

16. [4n]-heptalenes according to claim 15, whereby, $C^1$ and $C^2$ represent independently from each other a hydrogen atom, a methyl group, a phenyl group, an ethyl ester group, a methyl ester group, a (E)-PhCH=CH-group, a (E)-4-MeOC$_6$H$_4$CH=CH-group, a (E)-4-ClC$_6$H$_4$CH=CH-group, a 4-MeOC$_6$H$_4$-group, a —CH=CH—CH=CH—C$_6$H$_5$ group, a —CH=CH—C$_6$H$_4$NO$_2$-4 group, a —CH=CH—C$_6$H$_4$OMe-4 group, with the proviso that a heptalene being substituted by a methyl ester group at the position 1, a —CH=CH—CH=CH—C$_6$H$_5$ group at the positions 2 and 5, an isopropyl group at the position 7 and a methyl group at the position 10 is excluded.

17. [4n]-heptalenes according to claim 15, whereby said further substituents R are selected from the group comprising substituted or unsubstituted C$_1$–C$_{12}$alkyl groups or photoactive diazo-containing groups.

18. Method for the preparation of substituted heptalenes of the formula (I) or (II), according to claim 15

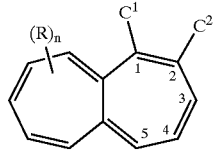

(I)

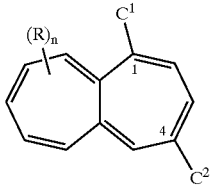

(II)

whereby $C^1$, $C^2$, R and n are as defined in claim 26, comprising the steps of (a) obtaining a heptalene-dicarboxylate by a reaction of a correspondingly substituted azulene with acetylenedicarboxylate, and optionally (b) transforming at least one carboxylic group or another substituent that was entered by the preliminary Diels-Alder reaction into the desired conjugated substituent having an extended π-electron system.

19. Method according to claim 18, whereby a heptalene-4,5-dicarboxylate carrying a methyl substituent at the position 1 of the heptalene ring is obtained.

20. Method according to claim 18, further comprising a step (c) wherein at least one of the carboxolate groups within the heptalene ring is replaced by a conjugated substituent containing an extended π-electron system.

21. Method according to claim 20, wherein the carboxylate group at the position 4 of the heptalene ring is replaced by a conjugated substituent containing an extended π-electron system.

22. An optical storage device comprising at least one substituted [4n]-annulene according to claim 15.

23. A non-linear optical device comprising at least one substituted [4n]-annulene according to claim 15.

24. Substituted [4n]-annulenes according to claim 15, wherein at least one of the groups $C^1$, $C^2$ or R is a group —COO—(CH$_2$)$_n$OH, a group —COO—(CH$_2$)$_n$OOC—C(CH$_3$)=CH$_2$ or a group —COO—(CH$_2$)$_n$C$_6$H$_4$-4-CH=CH$_2$ wherein n≧2.

* * * * *